US011020464B2

(12) United States Patent
Shimamura et al.

(10) Patent No.: US 11,020,464 B2
(45) Date of Patent: Jun. 1, 2021

(54) IMMUNOGENIC COMPOSITION TARGETING S100A9

(71) Applicants: OSAKA UNIVERSITY, Suita (JP); FUNPEP CO., LTD., Ibaraki (JP)

(72) Inventors: Munehisa Shimamura, Suita (JP); Tomohiro Kawano, Suita (JP); Hironori Nakagami, Suita (JP); Ryuichi Morishita, Suita (JP); Hideki Mochizuki, Suita (JP); Akiko Tenma, Ibaraki (JP); Takako Ehara, Ibaraki (JP)

(73) Assignees: OSAKA UNIVERSITY, Suita (JP); FUNPEP CO., LTD., Ibaraki (JP)

( * ) Notice: Subject to any disclaimer, the term of this patent is extended or adjusted under 35 U.S.C. 154(b) by 0 days.

(21) Appl. No.: 16/486,768

(22) PCT Filed: Feb. 20, 2018

(86) PCT No.: PCT/JP2018/006082
§ 371 (c)(1),
(2) Date: Oct. 14, 2019

(87) PCT Pub. No.: WO2018/155457
PCT Pub. Date: Aug. 30, 2018

(65) Prior Publication Data
US 2020/0023045 A1 Jan. 23, 2020

(30) Foreign Application Priority Data
Feb. 21, 2017 (JP) .............................. JP2017-030327

(51) Int. Cl.
| A61K 39/00 | (2006.01) |
| A61P 7/02 | (2006.01) |
| A61P 9/10 | (2006.01) |
| A61K 39/39 | (2006.01) |
| A61K 47/42 | (2017.01) |
| C07K 14/435 | (2006.01) |

(52) U.S. Cl.
CPC ...... *A61K 39/0005* (2013.01); *A61K 39/0003* (2013.01); *A61K 39/39* (2013.01); *A61K 47/42* (2013.01); *A61P 7/02* (2018.01); *A61P 9/10* (2018.01); *C07K 14/43504* (2013.01)

(58) Field of Classification Search
None
See application file for complete search history.

(56) References Cited

U.S. PATENT DOCUMENTS

| 7,081,345 B1 | 7/2006 | Roecklin et al. |
| 2006/0223121 A1 | 10/2006 | Roecklin et al. |
| 2015/0210768 A1 | 7/2015 | Roth et al. |
| 2019/0105388 A1 | 4/2019 | Nakagami et al. |

FOREIGN PATENT DOCUMENTS

| JP | 2003-509340 A | 3/2003 |
| JP | 2015-533485 A | 11/2015 |
| WO | WO 2017/164409 A1 | 9/2017 |

OTHER PUBLICATIONS

Houghten et al. (Vaccines, 1986, Edited by Fred Brown: Cold Spring Harbor Laboratory) (Year: 1986).*
Japanese Patent Office, International Preliminary Report on Patentability in International Patent Application No. PCT/JP2018/006082 (dated Aug. 27, 2019).
Bushnell et al., "Secondary preventive medication persistence and adherence 1 year after stroke," *Neurology*, 77: 1182-1190 (2011).
Dann et al., "Platelet-Derived MRP-14 Induces Monocyte Activation in Patients With Symptomatic Peripheral Artery Disease," *Journal of the American College of Cardiology*, 71(1): 53-65 (2018).
Glader et al., "Persistent Use of Secondary Preventive Drugs Declines Rapidly During the First 2 Years After Stroke," *Stroke*, 41: 397-401 (2010).
Ito et al., "Non-taking oral antithrombotic agents in patients with ischemic stroke," *Clinical Neurology*, 51: 35-37 (2011).
Wang et al., "Myeloid-related protein-14 regulates deep vein thrombosis," *JCI Insight*, 2(11): e91356 (Jun. 2, 2017).
Wang et al., "Platelet-derived S100 family member myeloid-related protein-14 regulates thrombosis," *The Journal of Clinical Investigation*, 124(5): 2160-2171 (2014).
Japanese Patent Office, International Search Report in International Patent Application No. PCT/JP2018/006082 (dated Apr. 3, 2018).
Kawano et al., "Therapeutic Vaccine Against S100A9 (S100 Calcium-Binding Protein A9) Inhibits Thrombosis Without Increasing the Risk of Bleeding in Ischemic Stroke in Mice," *Hypertension*, 72(6): 1355-1364 (2018).
Keng et al., "Intravenous thrombolysis in acute ischemic stroke: Perspective from single center experience in Malaysia," *J. Neurological Sci.*, 381: 866, Abstract 2411 (2017).

* cited by examiner

*Primary Examiner* — Padmavathi Baskar
(74) *Attorney, Agent, or Firm* — Leydig, Voit & Mayer, Ltd.

(57) ABSTRACT

Provided is an immunogenic composition comprising an antigenic peptide capable of inducing production of a neutralizing antibody against S100A9 and a carrier protein. The immunogenic composition can be used as a highly safe antithrombotic vaccine having antithrombotic effect without a long-term bleeding risk and is useful for the prevention of a disease associated with thrombus formation in which platelet aggregation is involved, particularly for the prevention of recurrent ischemic stroke.

20 Claims, 14 Drawing Sheets

Specification includes a Sequence Listing.

1: Marker
2: recombinant S100A9
3: recombinant S100A8

IMMUNOGENIC COMPOSITION TARGETING S100A9

CROSS-REFERENCE TO RELATED APPLICATIONS

This patent application is the U.S. national phase of International Patent Application No. PCT/JP2018/006082, filed Feb. 20, 2018, which claims the benefit of Japanese Patent Application No. 2017-030327, filed on Feb. 21, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 5,681 bytes ASCII (Text) file named "744682SequenceListing.txt," created Aug. 16, 2019.

TECHNICAL FIELD

The present invention relates to an immunogenic composition targeting S100A9.

BACKGROUND ART

Long-term treatment with antiplatelet agents, such as aspirin, a combination drug of aspirin and sustained-release dipyridamole, and clopidogrel, is important to prevent secondary stroke in patients with noncardioembolic stroke or transient ischemic attack. However, a recent study in Sweden reported that 26.3% of patients discontinued antiplatelet administration within 2 years (Non Patent Literature 1). In a study in the United States, discontinuation of antiplatelet administration within 1 year was reported in 22.5% of aspirin-treated patients, 43.8% of aspirin/dipyridamole-treated patients, and 35.8% of clopidogrel-treated patients (Non Patent Literature 2). Also in Japan, about 40% of patients diagnosed as recurrent ischemic stroke reportedly discontinued antiplatelet medication (Non Patent Literature 3).

Under such circumstances, in order to prevent recurrence of ischemic stroke, the development of a long-acting and highly cost-effective antiplatelet therapy is desired. From such a viewpoint, vaccines are a promising approach because they can provide long-lasting preventive effect without the need of daily administration and are thus cost-effective. Vaccines have traditionally been used to prevent infections, and in recent years, been applied to a broader range of diseases including general adult diseases such as hypertension and diabetes. However, vaccines for use in antithrombotic therapy have not yet been reported. An obstacle for the development of antithrombotic vaccines is their long-term increased risk of bleeding including fatal intracranial bleeding and gastrointestinal bleeding.

CITATION LIST

Non Patent Literature

Non Patent Literature 1:
Glader, E. L., Sjolander, M., Eriksson, M. & Lundberg, M. Persistent use of secondary preventive drugs declines rapidly during the first 2 years after stroke. Stroke 41, 397-401 (2010)

Non Patent Literature 2:
Bushnell, C. D., et al. Secondary preventive medication persistence and adherence 1 year after stroke. Neurology 77, 1182-1190 (2011)

Non Patent Literature 3:
Yasuyuki Ito, et al., Non-taking oral antithrombotic agents in patients with ischemic stroke. Clinical Neurology, vol. 51, 35-37 (2011)

SUMMARY OF INVENTION

Technical Problem

An object of the present invention is to provide a highly safe immunogenic composition having antithrombotic effect without a long-term bleeding risk.

Solution to Problem

The present invention includes the following to achieve the above-mentioned object.

[1] An immunogenic composition comprising an antigenic peptide capable of inducing production of a neutralizing antibody against S100A9 and a carrier protein.

[2] The composition according to the above [1], wherein the antigenic peptide consists of an amino acid sequence that is identical or substantially identical to an amino acid sequence of contiguous 7 or more amino acids within the amino acid sequence of residues 1 to 16 of SEQ ID NO: 2; an amino acid sequence that is identical or substantially identical to an amino acid sequence of contiguous 7 or more amino acids within the amino acid sequence of residues 21 to 33 of SEQ ID NO: 2; or an amino acid sequence that is identical or substantially identical to an amino acid sequence of contiguous 7 or more amino acids within the amino acid sequence of residues 95 to 114 of SEQ ID NO: 2.

[3] The composition according to the above [1], wherein the antigenic peptide consists of an amino acid sequence that is identical or substantially identical to the amino acid sequence of SEQ ID NO: 1.

[4] The composition according to the above [1] or [2], wherein the antigenic peptide consists of an amino acid sequence that is identical or substantially identical to the amino acid sequence of any of SEQ ID NOs: 6 to 20.

[5] The composition according to any one of the above [1] to [4], wherein the carrier protein is keyhole limpet hemocyanin.

[6] The composition according to any one of the above [1] to [5], further comprising an adjuvant.

[7] The composition according to any one of the above [1] to [6] for use in prevention of thrombus formation.

[8] The composition according to any one of the above [1] to [6] for use as an antithrombotic vaccine.

[9] The composition according to any one of the above [1] to [8] for use in prevention of cerebral infarction, myocardial infarction, arteriosclerosis obliterans, angina, or thrombocytosis.

[10] The composition according to any one of the above [1] to [8] for use in prevention of recurrent ischemic stroke.

[11] The composition according to any one of the above [1] to [6] for use in prevention or treatment of a chronic inflammatory disease in which S100A9 and CD36 are involved.

[12] The composition for use according to the above [11], wherein the chronic inflammatory disease in which S100A9 and CD36 are involved is arteriosclerosis, nonalcoholic fatty liver disease, nonalcoholic steatohepatitis, or Alzheimer-type dementia.

Advantageous Effects of Invention

The present invention provides a highly safe immunogenic composition having antithrombotic effect without a long-term bleeding risk.

BRIEF DESCRIPTION OF DRAWINGS

FIG. 10A shows microscopic images of representative wells of the indicated groups, and FIG. 10B shows the results of the measurement of the number of colored spots.

FIG. 14A shows the results for a KLH-administered mouse, and FIG. 14B shows the results for an SA9001-K-vaccinated mouse.

FIG. 15A shows the results for a KLH-administered mouse, and FIG. 15B shows the results for an SA9001-K-vaccinated mouse.

FIG. 19A shows the results of the measurement of the antibody titer against a conjugate of a human S100A9 antigenic peptide and BSA, and FIG. 19B shows the results of the measurement of the antibody titer against a recombinant human S100A9.

DESCRIPTION OF EMBODIMENTS

Figure 1:
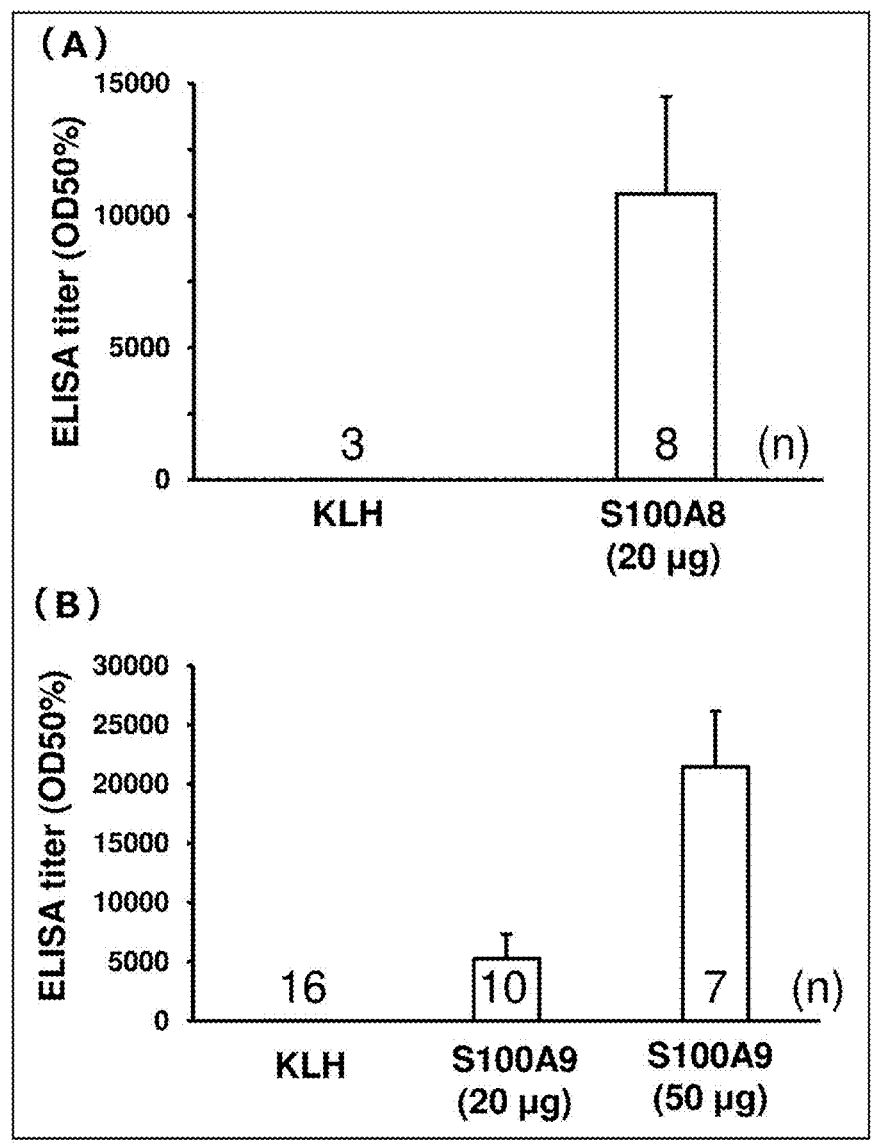
FIG. 1A shows the results of ELISA for the measurement of the antibody titer against S100A8 in the sera of mice given a conjugate (SA8001-K) vaccine of a mouse S100A8 antigenic peptide (ASHKDSHKE, SEQ ID NO: 5) and keyhole limpet hemocyanin (KLH).
FIG. 1B shows the results of ELISA for the measurement of the antibody titer against S100A9 in the sera of mice given a conjugate (SA9001-K) vaccine of a mouse S100A9 antigenic peptide (GHSHGKGCGK, SEQ ID NO: 3) and keyhole limpet hemocyanin (KLH).

The present invention provides an immunogenic composition comprising an antigenic peptide capable of inducing production of a neutralizing antibody against S100A9 and a carrier protein.

S100 proteins are a family of cell-type-specifically expressed calcium binding proteins having two EF-hands, and 20 subfamilies are identified so far. S100A9 (also called MRP14) is a member of low-molecular-weight calcium binding S100 proteins, and S100A9 and S100A8 (also called MRP8) are usually co-expressed and form a heterodimer. A S100A8/A9 complex is known to be associated with various inflammatory diseases. In addition, an increased serum S100A8/A9 complex level is observed in patients with various inflammatory diseases including giant cell arteritis, cystic fibrosis, rheumatoid arthritis, psoriasis, atopic dermatitis, chronic inflammatory bowel disease, chronic bronchitis, some malignant tumors, and autoimmune disease.

The antigenic peptide capable of inducing production of a neutralizing antibody against S100A9 can be designed based on the amino acid sequence of S100A9. The amino acid sequences of S100A9 proteins of major mammals are available from known databases (NCBI etc.). For example, the amino acid sequence of human S100A9 (SEQ ID NO: 2) is deposited in NCBI with the accession number NP_002956, and the amino acid sequence of mouse S100A9 (SEQ ID NO: 4) is deposited in NCBI with the accession number CAC14292.

The antigenic peptide capable of inducing production of a neutralizing antibody against S100A9 is not particularly limited as long as the antigenic peptide is an antigenic fragment of human S100A9. Preferably, the antigenic peptide is a peptide consisting of an amino acid sequence that is identical or substantially identical to an amino acid sequence of contiguous 7 or more amino acids within the amino acid sequence of residues 1 to 16 of SEQ ID NO: 2; a peptide consisting of an amino acid sequence that is identical or substantially identical to an amino acid sequence of contiguous 7 or more amino acids within the amino acid sequence of residues 21 to 33 of SEQ ID NO: 2; or a peptide consisting of an amino acid sequence that is identical or substantially identical to an amino acid sequence of contiguous 7 or more amino acids within the amino acid sequence of residues 95 to 114 of SEQ ID NO: 2.

The amino acid sequence that is identical or substantially identical to an amino acid sequence of contiguous 7 or more amino acids within the amino acid sequence of residues 1 to 16 of SEQ ID NO: 2 preferably includes an amino acid sequence that is identical to the amino acid sequence of residues 6 to 10 of SEQ ID NO: 2. Such an amino acid sequence may be, for example, MTCKMSQLER (SEQ ID NO: 6), TCKMSQLERN (SEQ ID NO: 7), CKMSQLERNI (SEQ ID NO: 8), KMSQLERNIE (SEQ ID NO: 9), MSQLERNIET (SEQ ID NO: 10), SQLERNIETI (SEQ ID NO: 11), or the like.

The amino acid sequence that is identical or substantially identical to an amino acid sequence of contiguous 7 or more amino acids within the amino acid sequence of residues 21 to 33 of SEQ ID NO: 2 may be, for example, QYSVKLGHPD (SEQ ID NO: 12), YSVKLGHPDT (SEQ ID NO: 13), SVKLGHPDTL (SEQ ID NO: 14), VKLGHPDTLN (SEQ ID NO: 15), or the like.

The amino acid sequence that is identical or substantially identical to an amino acid sequence of contiguous 7 or more amino acids within the amino acid sequence of residues 95 to 114 of SEQ ID NO: 2 preferably includes an amino acid sequence that is identical to the amino acid sequence of residues 102 to 106 of SEQ ID NO: 2. Such an amino acid sequence may be, for example, GDEGPGHHHK (SEQ ID NO: 16), DEGPGHHHKP (SEQ ID NO: 17), EGPGHHHKPG (SEQ ID NO: 18), GPGHHHKPGL (SEQ ID NO: 19), PGHHHKPGLG (SEQ ID NO: 20), GHHHKPGLGE (SEQ ID NO: 1), or the like.

The antigenic peptide capable of inducing production of a neutralizing antibody against S100A9 is more preferably a peptide consisting of an amino acid sequence that is identical or substantially identical to the amino acid sequence of SEQ ID NO: 1 (GHHHKPGLGE), and still more preferably a peptide consisting of the amino acid sequence of SEQ ID NO: 1.

The antigenic peptide capable of inducing production of a neutralizing antibody against S100A9 is not limited to a peptide consisting of a sequence that is identical to a partial sequence of the amino acid sequence of human S100A9 (SEQ ID NO: 2) and may be a peptide consisting of an amino acid sequence that is substantially identical to a partial sequence of the amino acid sequence of human S100A9 (SEQ ID NO: 2). For example, the amino acid sequence that is substantially identical to the amino acid sequence of SEQ ID NO: 1 may be an amino acid sequence that is identical to the amino acid sequence of SEQ ID NO: 1 except for having 1 or 2 amino acid deletions, substitutions, or additions and is capable of inducing production of a neutralizing antibody against S100A9. Preferred is an amino acid sequence that is identical to the amino acid sequence of SEQ ID NO: 1 except for having one amino acid deletion, substitution, or addition and is capable of inducing production of a neutralizing antibody against S100A9. A specific example of such an amino acid sequence may be an amino acid sequence having one amino acid (for example, cysteine) added to the N- or C-terminus for conjugation to a carrier protein via a linker.

In the case where an experiment using a laboratory animal (mouse etc.) is performed to examine the effects of the immunogenic composition of the present invention, it is preferable to use an amino acid sequence of the laboratory animal corresponding to the antigenic peptide sequence of human S100A9 in the experiment. The amino acid sequence of S100A9 of the laboratory animal to be used is available from known databases (NCBI etc.), and by alignment of the amino acid sequence with the human counterpart, the antigenic peptide sequence of the laboratory animal can be designed. The mouse antigenic peptide sequence corresponding to the above-mentioned human antigenic peptide sequence represented by SEQ ID NO: 1 is GHSHGKGCGK (SEQ ID NO: 3). When monkeys are used as a laboratory animal, the effects of the immunogenic composition of the present invention comprising the antigenic peptide of human S100A9 can be examined.

The carrier protein is not particularly limited and can be selected as appropriate from known carrier proteins that can be used for vaccines. Examples of the known carrier protein include albumin, ovalbumin, keyhole limpet hemocyanin (KLH), *Pseudomonas aeruginosa* exotoxin, tetanus toxin, ricin toxin, diphtheria toxin, cholera toxin, heat-labile enterotoxin, epidermal growth factor, fibroblast growth factor, transferrin, platelet-derived growth factor, poly-L-lysine, poly-L-glutamine, mannose-6-phosphate, and hepatitis B viral core protein. In particular, keyhole limpet hemocyanin (KLH) is preferable.

The antigenic peptide is preferably conjugated to the carrier protein. The antigenic peptide and the carrier protein may be conjugated directly like a fusion protein or via a linker (used as a synonym for a spacer). The linker is not particularly limited as long as it is capable of connecting the antigenic peptide with the carrier protein. Examples of the linker include aminocarboxylic acids such as β-aminoalanine, γ-aminobutyric acid, ε-aminocaproic acid, 7-aminoheptanoic acid, 12-aminolauric acid, glutamic acid, and p-aminobenzoic acid. Other examples include L-amino acids, which are present in naturally occurring proteins, and D-isomers thereof. In addition, crosslinkers, such as EMCS (N-(6-maleimidocaproyloxy)succinimide), glutaraldehyde, and Sulfo-GMBS (N-γ-maleimidobutyryl-oxysulfosuccinimide ester), can be used.

In the case where KLH is used as the carrier protein and the antigenic peptide has no lysine (Lys;K), glutaraldehyde can preferably be used as the linker. Even in the case where the antigenic peptide has lysine, as long as the lysine is located only at the N- or C-terminus of the antigenic peptide, glutaraldehyde can preferably be used as the linker. In the case where the antigenic peptide has lysine at a site other than the N- or C-terminus, it is preferable to introduce cysteine (Cys;C) into the N- or C-terminus of the antigenic peptide and/or to use EMCS for conjugation of the antigenic peptide and the carrier protein. Alternatively, regardless of the sequence of the antigenic peptide, the conjugation of the antigenic peptide and the carrier protein can be achieved using Sulfo-GMBS after cysteine introduction into the C-terminus of the antigenic peptide.

The immunogenic composition of the present invention may further comprise one or more adjuvants. The adjuvant can be selected as appropriate from known adjuvants. Specific examples of the known adjuvant include aluminum adjuvants (for example, aluminum salts such as aluminum hydroxide, aluminum phosphate and aluminum sulfate, or any combination thereof), complete or incomplete Freund's adjuvant, TLR ligands (for example, CpG, Poly(I:C), Pam3CSK4, etc.), BAY, DC-chol, pcpp, monophosphoryl lipid A, QS-21, cholera toxin, and formylmethionyl peptides. Preferred are aluminum adjuvants.

Administration of the immunogenic composition of the present invention to an animal enables effective prevention of thrombus formation in which platelet aggregation is involved. Therefore, the immunogenic composition of the present invention is suitable for use as an antithrombotic vaccine.

The immunogenic composition of the present invention is suitable for use in prevention of diseases associated with thrombus formation in which platelet aggregation is involved, such as cerebral infarction, myocardial infarction, arteriosclerosis obliterans, angina, and thrombocytosis. In addition, the immunogenic composition of the present invention is suitable for use in prevention of recurrent ischemic stroke.

The immunogenic composition of the present invention is suitable for use in prevention or treatment of a chronic inflammatory disease in which S100A9 and CD36 are involved. Examples of the chronic inflammatory disease in which S100A9 and CD36 are involved include arteriosclerosis, nonalcoholic fatty liver disease (NAFLD), nonalcoholic steatohepatitis (NASH), and Alzheimer-type dementia. The immunogenic composition of the present invention is preferable for use in prevention or treatment of arteriosclerosis.

The immunogenic composition of the present invention can be orally or parenterally administered. The parenteral administration includes intraperitoneal administration, subcutaneous administration, intracutaneous administration, intramuscular administration, intravenous administration, intranasal administration, transdermal administration, transmucosal administration, sublingual administration, and inhalation administration. Preferred is parenteral administration, and more preferred are intracutaneous administration, subcutaneous administration, and intramuscular administration.

For the formulation of the immunogenic composition of the present invention, the antigenic peptide capable of inducing production of a neutralizing antibody against S100A9, the carrier protein, a pharmaceutically acceptable carrier and if needed an additive are blended and formed into a dosage form. Specific examples of the dosage form include oral preparations such as tablets, coated tablets, pills, powders, granules, capsules, solutions, suspensions, and emulsions; and parenteral preparations such as injections, infusions, suppositories, ointments, and patches. The amount of the carrier or the additive to be used is determined as appropriate based on the range of amount conventionally used in the pharmaceutical field. The carrier or the additive that can be used is not particularly limited, and examples include various carriers such as water, physiological saline, other aqueous solvents, and aqueous or oily bases; and various additives such as fillers, binders, pH adjusters, disintegrants, absorption enhancers, lubricants, colorants, corrigents, and fragrances.

Examples of the additive used for solid oral preparations include excipients such as lactose, mannitol, glucose, microcrystalline cellulose, and corn starch; binders such as hydroxypropyl cellulose, polyvinylpyrrolidone, and magnesium aluminometasilicate; dispersants such as corn starch; disintegrants such as calcium carboxymethyl cellulose; lubricants such as magnesium stearate; solubilizing agents such as glutamic acid and aspartic acid; stabilizers; water soluble polymers including celluloses such as hydroxypropyl cellulose, hydroxypropylmethyl cellulose, and methyl cellulose, and synthetic polymers such as polyethylene glycol, polyvinylpyrrolidone, and polyvinyl alcohol; sweeteners such as white sugar, powder sugar, sucrose, fructose, glucose, lactose, reduced malt sugar syrup (maltitol syrup), reduced malt sugar syrup powder (maltitol syrup powder), high-glucose corn syrup, high-fructose corn syrup, honey, sorbitol, maltitol, mannitol, xylitol, erythritol, aspartame, saccharin, and saccharin sodium; and coating agents such as white sugar, gelatin, hydroxypropyl cellulose, and hydroxypropylmethyl cellulose phthalate.

The formulation of liquid oral preparations involves dissolution, suspension or emulsification in a generally used diluent. Examples of the diluent include purified water, ethanol, and a mixture thereof. The oral liquid preparation may further contain a wetting agent, a suspending agent, an emulsifier, a sweetener, a flavoring agent, a fragrance, a preservative, a buffering agent, and/or the like.

Examples of the additive used for injections for parenteral administration include isotonizing agents such as sodium chloride, potassium chloride, glycerin, mannitol, sorbitol, boric acid, borax, glucose, and propylene glycol; buffering agents such as a phosphate buffer solution, an acetate buffer solution, a borate buffer solution, a carbonate buffer solution, a citrate buffer solution, a Tris buffer solution, a glutamate buffer solution, and an ε-aminocaproate buffer solution; preservatives such as methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, disodium edetate, boric acid, and borax; thickeners such as hydroxyethyl cellulose, hydroxypropyl cellulose, polyvinyl alcohol, and polyethylene glycol; stabilizers such as sodium hydrogen sulfite, sodium thiosulfate, disodium edetate, sodium citrate, ascorbic acid, and dibutylhydroxytoluene; and pH adjusters such as hydrochloric acid, sodium hydroxide, phosphoric acid, and acetic acid. The injection may further contain an appropriate solubilizer. Examples of the solubilizer include alcohols such as ethanol; polyalcohols such as propylene glycol and polyethylene glycol; and nonionic surfactants such as polysorbate 80, polyoxyethylene hydrogenated castor oil 50, lysolecithin, and Pluronic polyol. Liquid preparations such as injections can be preserved in a frozen state, or in a dried state after water removal by lyophilization etc. Lyophilized preparations can be reconstituted in distilled water for injection or the like just before use.

The immunogenic composition of the present invention can be administered to any animal (a human or a non-human animal) with an immune system. Examples of the animal include mammals such as humans, monkeys, cattle, horses, pigs, sheep, goats, dogs, cats, guinea pigs, rats, and mice; and birds such as chickens, ducks, and geese. Preferably, the immunogenic composition of the present invention is administered to a human child or adult.

In the administration of the immunogenic composition of the present invention, the dosing frequency and interval are not particularly limited. For example, the immunogenic composition may be administered once, or multiple times at intervals of about two days to about eight weeks. The dose of the immunogenic composition varies with the administration subject, the administration method, etc., but the dose of the antigenic peptide per administration is preferably about 0.01 µg to about 10 mg, more preferably about 0.1 µg to about 1 mg, and still more preferably about 1 µg to about 0.1 mg.

The immunogenic composition of the present invention was shown in an experiment using mice to provide a long-lasting immunity which enables production of an antibody against S100A9 for at least 2 months from the final administration and to provide a booster effect after subsequent additional administration (see Examples). In consideration of the problem that about 40% of patients diagnosed as recurrent ischemic stroke discontinued antiplatelet administration (Non Patent Literature 3), the immunogenic composition of the present invention, due to its long-lasting immunity and booster effect provided by additional administration, is expected as a very useful vaccine or medicament for prevention of recurrent stroke in patients with noncardioembolic stroke or transient ischemic attack.

The present invention further includes the following.

A method for preventing thrombus formation or preventing or treating a chronic inflammatory disease in which S100A9 and CD36 are involved, the method comprising administering the immunogenic composition of the present invention to an animal.

An immunogenic composition of the present invention for use in prevention of thrombus formation or in prevention or treatment of a chronic inflammatory disease in which S100A9 and CD36 are involved.

Use of the immunogenic composition of the present invention for production of a vaccine or a medicament for prevention of thrombus formation or for prevention or treatment of a chronic inflammatory disease in which S100A9 and CD36 are involved.

The immunogenic composition of the present invention can prolong the occlusion time in a dose dependent manner without affecting hemostatic parameters or inducing detrimental autoimmune responses. Moreover, the immunogenic composition of the present invention provides a long-lasting immunity which enables production of an anti-S100A9 antibody for at least 2 months after administration and provides a booster effect after subsequent additional administration to further prolong the occlusion time. Therefore, the immunogenic composition of the present invention is useful for prevention of thrombus formation in diseases such as cerebral infarction, myocardial infarction, arteriosclerosis obliterans, and thrombocytosis, and in particular, is very useful for prevention of recurrent stroke in ischemic stroke patients having difficulty in daily intake of an oral antiplatelet agent.

EXAMPLES

Hereinafter, the present invention will be described in detail by examples, but the present invention is not limited thereto. Animal experiments using mice in the Examples given below were conducted after approval by the Ethics Committee for Animal Experiments of Osaka University Graduate School of Medicine. Animal experiments using monkeys were conducted after approval by the Review Board for Animal Experiments of CMIC Pharma Science Co., Ltd.

Example 1

Antibody Production by Vaccine Administration (1) Design and Synthesis of Vaccines The amino acid sequence of the C-terminal region of mouse S100A9 (residues 104 to 113, GHSHGKGCGK, SEQ ID NO: 3) was selected as an antigenic peptide of mouse S100A9. The amino acid sequence of the C-terminal region of mouse S100A8 (residues 81 to 89, ASHKDSHKE, SEQ ID NO: 5) was selected as an antigenic peptide of mouse S100A8. For the production of each antigenic peptide, a protected peptide-bound resin was synthesized by the Fmoc method using a fully-automatic solid-phase synthesizer according to the protocol described in Solid Phase Peptide Synthesis, Pierce (1984); Fmoc Solid Synthesis: A Practical Approach, Oxford University Press (2000); The Fifth Series of Experimental Chemistry (Jikken Kagaku Kouza), vol. 16, Synthesis of Organic Compounds IV; or the like. To the protected peptide-bound resin, trifluoroacetic acid (TFA) and a scavenger (a mixture of thioanisole, ethanedithiol, phenol, triisopropylsilane, water and the like) were added for cleavage of the protected peptide from the resin and subsequent deprotection. Thus, the peptide of interest was obtained as a crude product. For the purification of the peptide, the crude product was applied to a reverse-phase HPLC column (ODS), and elution was performed with a gradient of 0.1% $TFA-H_2O/CH_3CN$. The fractions containing the peptide of interest were combined and freeze-dried, and the peptide of interest was obtained. The amino acid sequence of each synthesized peptide was confirmed with an amino acid sequencer.

The obtained antigenic peptide of mouse S100A9 (SEQ ID NO: 3) and the obtained antigenic peptide of mouse S100A8 (SEQ ID NO: 5) were separately conjugated to KLH (keyhole limpet hemocyanin, Peptide Institute, Inc.) via EMCS (N-(6-maleimidocaproyloxy)succinimide). Hereinafter, the conjugate of the antigenic peptide of mouse S100A9 (SEQ ID NO: 3) and KLH is called "SA9001-K", and the conjugate of the antigenic peptide of mouse S100A8 (SEQ ID NO: 5) and KLH is called "SA8001-K".

(2) Experimental Method

Seven-week-old male C57BL/6J mice were purchased from CLEA Japan, Inc. The mice were assigned to 4 groups: an SA8001-K vaccine group (20 µg (antigenic peptide)/mouse), an SA9001-K vaccine low-dose group (20 µg (antigenic peptide)/mouse), an SA9001-K vaccine high-dose group (50 µg (antigenic peptide)/mouse), and a KLH group as the control. The mice assigned to the KLH group were given KLH in an amount equal to the KLH content of the conjugate. SA8001-K, SA9001-K, and KLH were separately mixed with an equal volume of Freund's adjuvant (Wako Pure Chemical Industries, Ltd.) before subcutaneous administration. Complete Freund's adjuvant was used at the first administration, and incomplete Freund's adjuvant was used at the second and further administrations. The mice assigned to the SA9001-K vaccine low-dose group or the SA9001-K vaccine high-dose group were given the vaccines 3 times in total (Days 0, 14, and 28). The mice assigned to the SA8001-K vaccine group were given the vaccine twice in total (Days 0 and 14). Blood samples were collected from the tail vein at 2 weeks after the final administration (Day 28 for the SA8001-K vaccine group and Day 42 for the SA9001-K vaccine groups (both low dose and high dose)). The sera were separated and used as the samples in this example.

The antibody titer against S100A8 or S100A9 was measured by ELISA. More specifically, the measurement was performed using ELISA plates coated with a BSA-S100A8 conjugate (Peptide Institute) or a BSA-S100A9 conjugate (Peptide Institute). An HRP-conjugated anti-mouse IgG sheep antibody (NA931V, GE Healthcare) was used for antibody detection.

For the detection of an anti-S100A8 antibody and an anti-S100A9 antibody in the sera of the SA8001-K vaccine group, the SA9001-K vaccine high-dose group, and the KLH group, western blotting was used. More specifically, recombinant mouse S100A8 (Abcam) and recombinant mouse S100A9 (Abcam) were subjected to SDS-PAGE and then transferred on a PVDF membrane (Millipore). The blotted PVDF membrane was incubated with each serum and then with an HRP-conjugated anti-mouse IgG sheep antibody (NA931V, GE Healthcare). Chemiluminescent signals were captured with LAS 1000 camera (FUJIFILM Corporation) and analyzed by MultiGauge ver. 3.2 software (FUJIFILM Corporation). For the positive control, the blotted PVDF membrane was incubated with a commercial anti-mouse S100A8 antibody (R&D Systems) or a commercial anti-mouse S100A9 antibody (LifeSpan BioSciences, Inc.), and chemiluminescent signals were captured and analyzed similarly as above.

(3) Results

The results of the measurement of the antibody titers by ELISA are shown in FIGS. 1A and 1B. FIG. 1A shows the results for the SA8001-K vaccine group, and FIG. 1B shows the results for the SA9001-K vaccine low-dose group and the SA9001-K vaccine high-dose group. The antibody titer against S100A8 in the sera of the SA8001-K-vaccinated mice increased completely on Day 28. The antibody titer against S100A9 in the sera of the SA9001-K-vaccinated mice in both the low-dose and high-dose groups increased completely on Day 42.

Figure 2:
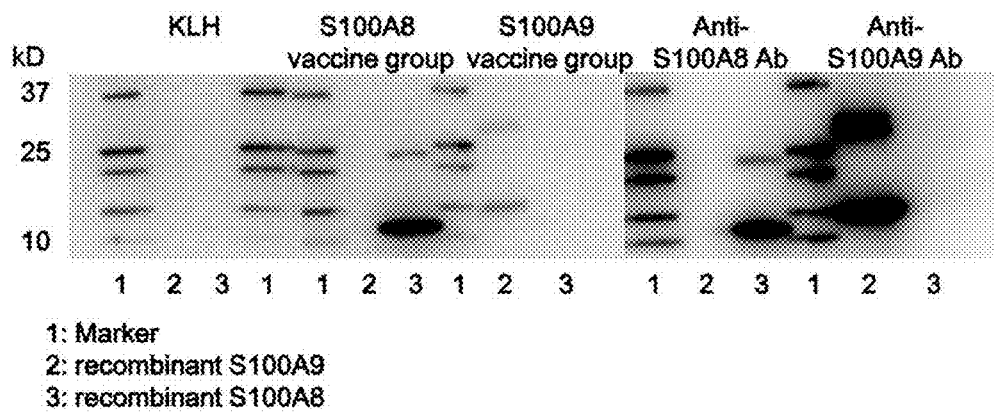
FIG. 2 shows the results of western blotting for the detection of an anti-S100A8 antibody in the serum of an SA8001-K-vaccinated mouse and an anti-S100A9 antibody in the serum of an SA9001-K-vaccinated mouse.

The results of the western blotting are shown in FIG. 2. The antibody reactive for S100A8 was detected in the serum in the SA8001-K vaccine group (S100A8 vaccine group in the figure), and the antibody reactive for S100A9 was detected in the serum of the SA9001-K vaccine group (S100A9 vaccine group in the figure).

Example 2

Examination of Effect Against Middle Cerebral Artery Occlusion (1) Experimental Method The mice in the SA8001-K vaccine group, the SA9001-K vaccine low-dose group, the SA9001-K vaccine high-dose group, and the KLH group of Example 1 were subjected to a middle cerebral artery occlusion test at 3 weeks after the final administration. Separately, a clopidogrel low-dose group (3 mg/kg) and a clopidogrel high-dose group (6 mg/kg) were prepared. For the clopidogrel groups, mice were given a mixture of physiological saline and Freund's adjuvant on the same schedule (Days 0, 14, and 28) as that for the SA9001-K vaccine group. Clopidogrel (Sanofi K.K.) was dissolved in water and orally administered to the mice for consecutive 2 days on the previous day and the day of the middle cerebral artery occlusion test.

A ferric chloride-induced thrombosis mouse model was produced according to the method of Karatas et al. (Karatas, H. et al., J Cereb Blood Flow Metab 31, 1452-1460, 2011) as a distal middle cerebral artery occlusion model. The specific procedure was as follows. Mice were anesthetized by inhalation of 1.4% isoflurane, and the body temperature was monitored with a rectal probe and maintained at 37.0±0.5° C. during surgery. Each mouse was placed in a stereotactic frame and underwent craniotomy using a high-speed drill (Leutor Mini Pen LP-120, Nihon Seimitsu Kikai Kosaku Co., Ltd.). Thereafter, a laser doppler blood flow meter (Unique Medical Co., Ltd.) was placed on the cranial bone to monitor the regional cerebral blood flow (rCBF). A piece of filter paper saturated with 20% ferric chloride was placed on the pia mater over the right distal middle cerebral artery for 3 minutes and then removed. The rCBF was continuously monitored for 30 minutes from the onset of injury. The occlusion time, which was defined as the time at which at least 5 minute-duration of 40% or more reduced rCBF from the baseline was confirmed, was recorded.

Histological examination of the middle cerebral artery was performed on non-perfused or perfusion-fixed brains. In the case of non-perfusion, the middle cerebral artery attached to the brain was collected 25 minutes after the ferric chloride exposure, fixed with 4% paraformaldehyde overnight, and embedded in paraffin. In the case of perfusion fixation, 25 minutes after the ferric chloride exposure, 20 mL of 0.1 M phosphate buffer and subsequently 20 mL of 4% paraformaldehyde were administered to mice under deep anesthesia from the cardiac apex. After that, the middle cerebral artery attached to the brain was collected and embedded in paraffin. In either case, the brain was cut into 3-μm-thick sections, and the sections were stained with hematoxylin and eosin.

(2) Results

Figure 3:
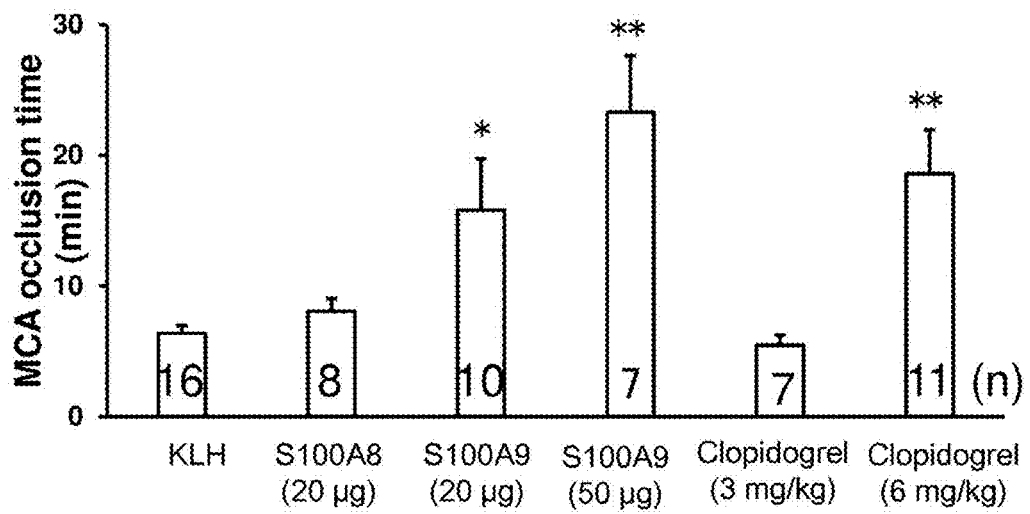
FIG. 3 shows the effect of an S100A8 vaccine and an S100A9 vaccine on the middle cerebral artery occlusion in distal middle cerebral artery occlusion model mice.

The results of the middle cerebral artery occlusion time are shown in FIG. 3. The middle cerebral artery occlusion time was significantly prolonged in the SA9001-K vaccine groups as compared with the KLH group (KLH group: 6.4±0.6 (minutes), SA9001-K vaccine low-dose group: 15.8±3.9 (minutes), $p<0.05$, SA9001-K vaccine high-dose group: 23.3±4.3 (minutes), $p<0.01$). The clopidogrel low-dose group showed no significant difference in the middle cerebral artery occlusion time as compared with the KLH group, but the clopidogrel high-dose group showed a significantly prolonged middle cerebral artery occlusion time (18.6±3.4 (minutes), $p<0.01$). In the SA8001-K vaccine group, no effect on the middle cerebral artery occlusion time was observed.

Figure 4:
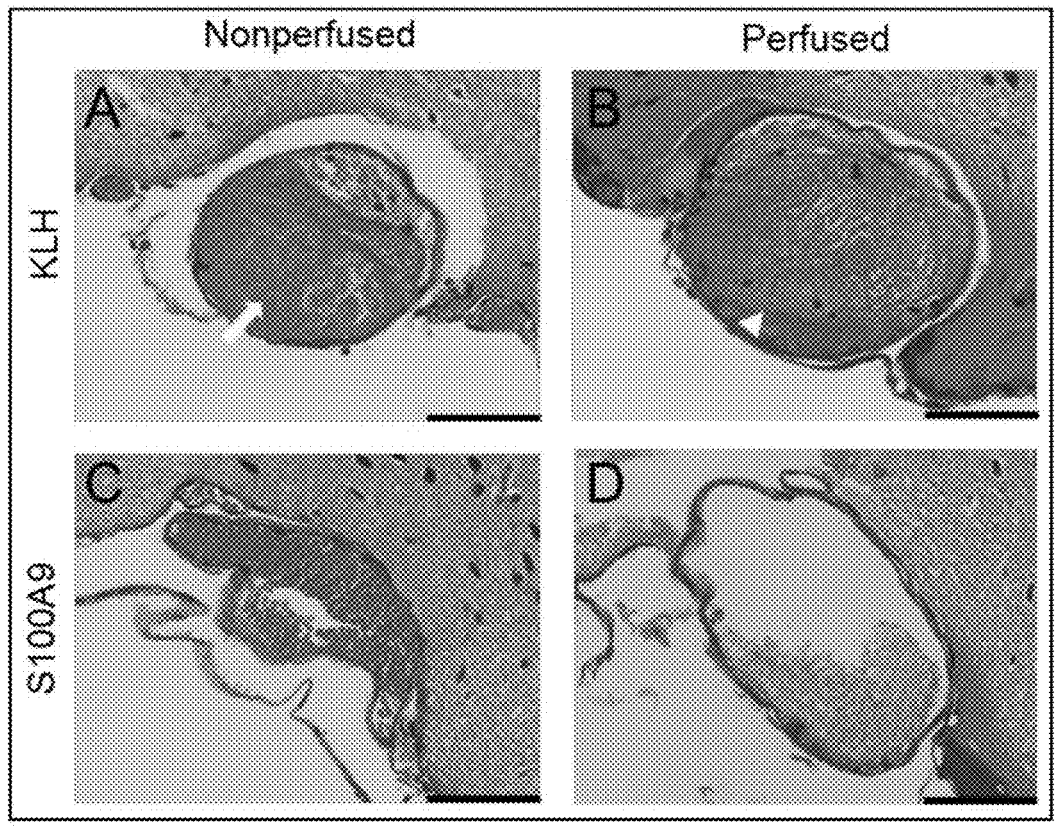
FIG. 4 shows the results of histopathological examination of the middle cerebral artery dissected from an SA9001-K-vaccinated mouse or a KLH-administered mouse exposed to ferric chloride for induction of thrombosis formation in the middle cerebral artery. The left panels show middle cerebral artery specimens of non-perfused brains, and the right panels show middle cerebral artery specimens of perfusion-fixed brains.

The results of the histopathological examination are shown in FIG. 4. In the figure, the left panels represent non-perfused specimens, and the right panels represent perfusion-fixed specimens. The top panels represent the KLH group and the bottom panels represent the SA9001-K vaccine high-dose group. In each panel, the scale bar marks 50 μm. As shown in the figure, the lumen was filled with a fibrin-platelet rich thrombus (arrow in FIG. 4A) in the non-perfused specimen of the KLH group, but not in the non-perfused specimen of the SA9001-K vaccine high-dose group. In the perfusion-fixed specimen of the KLH group, the lumen was occluded with thrombus (arrowhead in FIG. 4B). In contrast, in the perfusion-fixed specimen of the SA9001-K vaccine high-dose group, the lumen remained open although small thrombi were observed along the blood vessel wall.

These results show that thrombus formation is almost completely prevented, or even if formed, thrombus is fragile after S100A9 vaccination.

Example 3

Examination of Effect Against Platelet Thrombus Formation (1) Experimental Method The effect of the S100A9 vaccine against platelet thrombus formation was evaluated using blood samples collected from the mice in the SA9001-K vaccine high-dose group and the KLH group of Example 1. A physiological saline group was prepared as the negative control. For the physiological saline group, mice were given a mixture of physiological saline and Freund's adjuvant on the same schedule (Days 0, 14, and 28) as that for the SA9001-K vaccine group, and blood samples were collected at 2 weeks after the final administration.

A platelet thrombus formation assay was performed with an automated microchip flow-chamber system (Fujimori Kogyo Co., Ltd.) according to the method of Hosokawa et al. (Hosokawa, K. et al., Microvasc Res 83, 154-161, 2012). The specific procedure was as follows. The whole blood (350 µL) was treated with the anticoagulant hirudin (25 µg/mL) and perfused into a collagen-coated microchip at a shear rate of 1000 $s^{-1}$. After that, the thrombus area was quantified by computer-assisted imaging analysis (ImageJ version 1.48 and GIMP 2.8).

(2) Results

Figure 5:
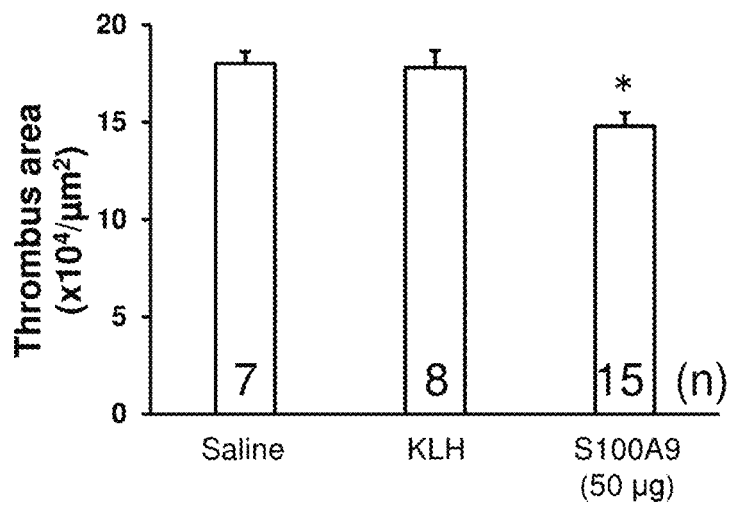
FIG. 5 shows the effect of an S100A9 vaccine against platelet thrombus formation.

The results are shown in FIG. 5. The platelet thrombus formation in the microchip flow-chamber system was significantly inhibited in the SA9001-K vaccine high-dose group as compared with the physiological saline group and the KLH group ($p<0.05$). These results show that the S100A9 vaccine inhibits platelet functions and thereby prevents platelet thrombus formation.

Example 4

Examination of Effect on Bleeding (1) Experimental Method

A tail bleeding assay was performed at 3 days after the middle cerebral artery occlusion test on the middle cerebral artery occlusion model mice of Example 2 in the SA9001-K vaccine high-dose group, the KLH group, and the clopidogrel high-dose group. The mice in the clopidogrel high-dose group were further given clopidogrel for consecutive 3 days from the day following the middle cerebral artery occlusion test to the day of the tail bleeding assay.

The tail bleeding assay was performed according to the method of Liu et al. (Liu, Y. et al., World J Exp Med 2, 30-36, 2012). The specific procedure was as follows. Mice were anesthetized by inhalation of 1.4% isoflurane and placed in a prone position. The distal 1-cm segment of the tail was amputated with a scalpel, and the tail was immediately immersed in a 50-mL tube containing physiological saline preheated at 37° C. Each mouse was monitored for 20 minutes, and the cumulative bleeding time within the 20-minute period was recorded.

(2) Results

Figure 6:
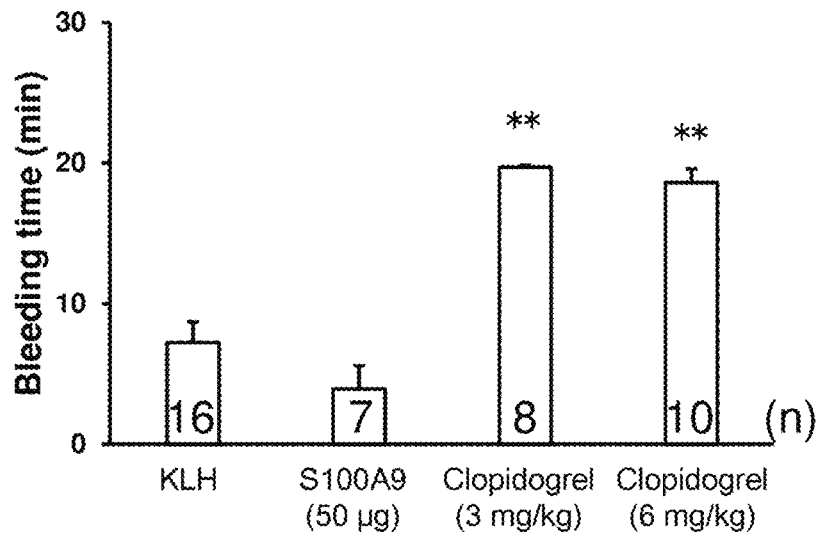
FIG. 6 shows the effect of an S100A9 vaccine on bleeding.

The results are shown in FIG. 6. No significant difference in the tail bleeding time was observed between the SA9001-K vaccine high-dose group and the KLH group. In contrast, the clopidogrel (3 mg/kg) group and the clopidogrel (6 mg/kg) group showed a significantly longer tail bleeding time as compared with the KLH group ($p<0.01$ each). These results show that the S100A9 vaccine does not affect bleeding.

Example 5

Examination of Effect Against Platelet Coagulation (1) Experimental Method

The effect of the S100A9 vaccine against platelet coagulation was evaluated using blood samples collected from the mice in the SA9001-K vaccine high-dose group and the KLH group of Example 1.

Blood samples were collected into tubes containing EDTA, and the platelet count was measured with the veterinary blood cell counter VetScan HM2 (Abaxis). The effect on coagulation activity was evaluated by measurement of the activated partial thromboplastin time (aPTT) and the prothrombin time (PT). Blood samples were collected into tubes containing sodium citrate and centrifuged at 1500 rpm at 4° C. for 15 minutes. The measurement of aPTT and PT was performed in KAC Co., Ltd.

(2) Results

Figure 7:
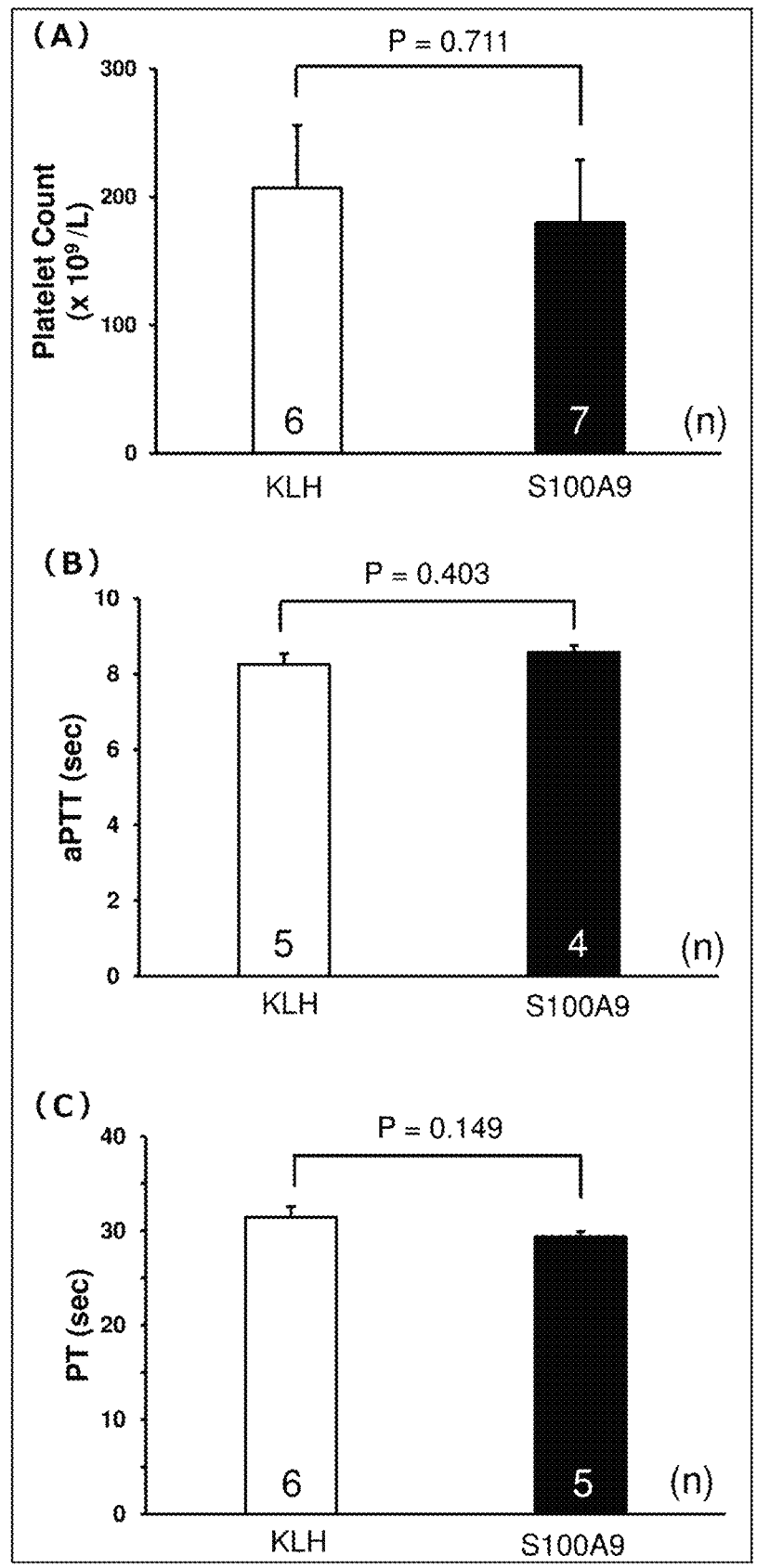
FIG. 7A shows the results of the measurement of the platelet count.
FIG. 7B shows the results of the measurement of the activated partial thromboplastin time (aPTT).
FIG. 7C shows the results of the measurement of the prothrombin time (PT).

The results are shown in FIGS. 7A to 7C. FIG. 7A shows the results of the platelet count, FIG. 7B shows the results of aPTT, and FIG. 7C shows the results of PT. The platelet count was comparable between the KLH group ($207\pm49\times10^9$ cells/L) and the SA9001-K vaccine high-dose group ($180\pm49\times10^9$ cells/L) ($p=0.711$). Similarly, no significant difference in either aPTT or PT was observed between the KLH group and the SA9001-K vaccine high-dose group ($p=0.403$ for aPTT, $p=0.149$ for PT). These results show that the S100A9 vaccine does not affect hemostasis.

Example 6

Examination of Effect on Serum S100A9 Level (1) Experimental Method

From the mice in the SA9001-K vaccine high-dose group and in the KLH group subjected to the middle cerebral artery occlusion test in Example 2, blood samples were collected and examined. More specifically, blood samples were collected before SA9001-K vaccination (at preimmunization), on Day 42 after the first administration (2 weeks after the 3rd vaccination), and at 3 days after the middle cerebral artery occlusion test. The serum S100A9 level in each blood sample was measured with the mouse S100A9 DuoSet ELISA Development kit (R&D Systems).

(2) Results

Figure 8:
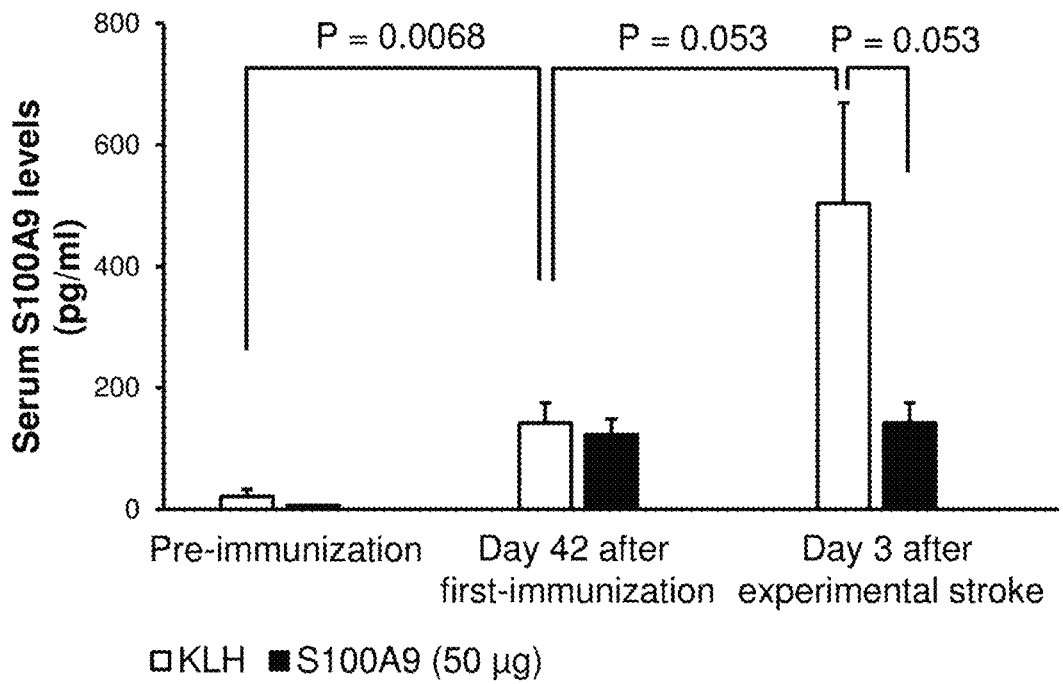
FIG. 8 shows the effect of an S100A9 vaccine on the serum S100A9 level.

The results are shown in FIG. 8. There was no significant difference in the serum S100A9 level either at preimmunization or on Day 42 after the first immunization between the KLH group and the SA9001-K vaccine high-dose group. The serum S100A9 level at 3 days after experimental stroke was increased in the KLH group. In contrast, the SA9001-K vaccine high-dose group showed a tendency to inhibit the increase in the serum S100A9 level although no statistically significant difference was found ($p=0.053$). These results indicate that the S100A9 vaccine is capable of reducing the serum S100A9 level and inhibiting platelet coagulation signaling induced by S100A9.

Example 7

Figure 9:
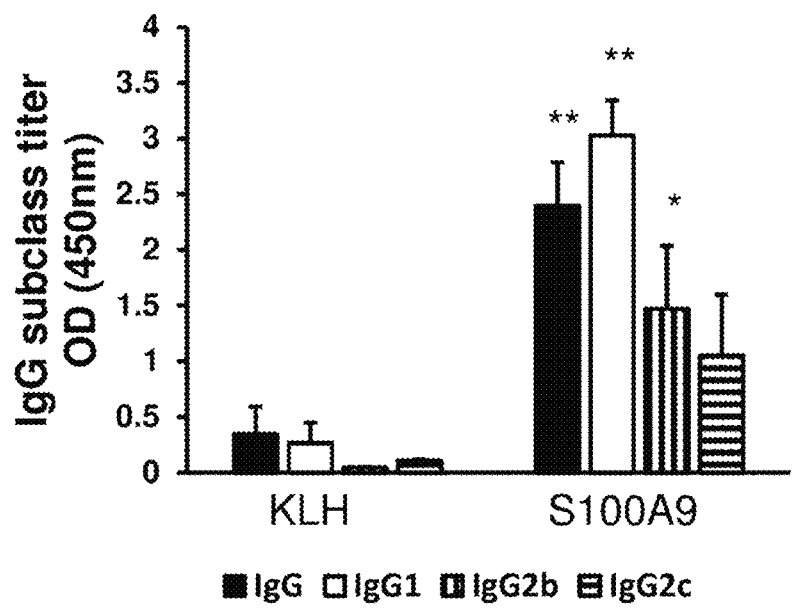
FIG. 9 shows the results of the measurement of the titer of each IgG subclass of the antibody induced by an S100A9 vaccine.

Evaluation of T-Cell Activation 7-1 Determination of IgG Subclass
(1) Experimental Method Blood samples were collected from the mice in the SA9001-K vaccine high-dose group and the KLH group of Example 1 on Day 42 after the first administration (2 weeks after the 3rd vaccination) and tested. The IgG subclass of the antibody induced by SA9001-K vaccination was determined by ELISA using anti-mouse IgG subclass-specific HRP-conjugated antibodies (IgG1, IgG2b, and IgG2c).
(2) Results The results are shown in FIG. 9. The ratio of IgG1:IgG2b in the anti-S100A9 antibody pool was larger than 1.0 in the SA9001-K vaccine group (1:250 dilution). These results show that the S100A9 vaccine induces Th2-type response (IgG1).

7-2 T-Cell Activation by S100A9 Vaccination
(1) Experimental Method

Figure 10:
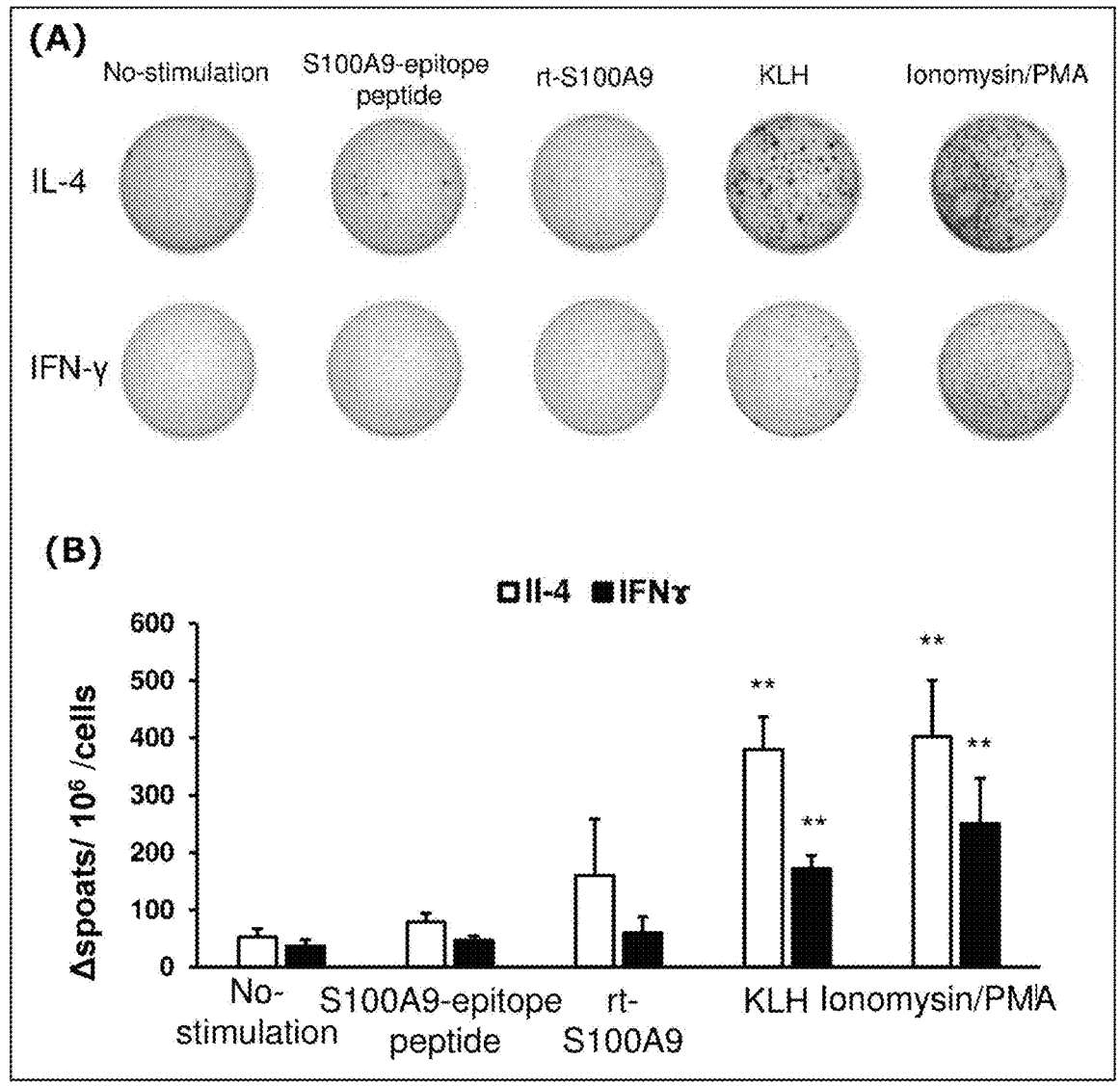
FIG. 10 shows the results of ELISPOT assay for T-cell activation in SA9001-K-vaccinated mouse splenocytes stimulated with an S100A9 antigenic peptide, a recombinant S100A9 protein, or KLH.

The production of IFN-γ and IL-4, which are cytokines related to Th1-type and Th2-type responses, respectively, was examined using splenocytes from the S100A9-vaccinated mice. Spleens were dissected from the mice in the SA9001-K vaccine high-dose group of Example 1 at 2 to 3 weeks after the final vaccination and subjected to an ELISPOT (enzyme-linked immunosorbent spot) assay. The ELISPOT assay was performed according to the method of Pang et al. (Pang, Z. et al., Proc Natl Acad Sci USA 111, E1256-1263, 2014). The specific procedure was as follows. Sterile 96-well ELISPOT plates (Millipore) were coated with an anti-mouse IFN-γ capture antibody or an anti-mouse IL-4 capture antibody and incubated at 4° C. overnight. After that, the plates were washed with PBS containing 0.05% Tween 20 (PBS-T) and then blocked with PBS containing 1% BSA and 5% (wt/vol) sucrose. Splenocyte suspensions were prepared from the dissected spleens, added to the plates ($10^6$ cells/well), and stimulated with 10 µg/mL of the S100A9 antigenic peptide (SEQ ID NO: 3), KLH, or a recombinant S100A9 protein at 37° C. for 48 hours. Ionomycin/PMA (phorbol 12-myristate 13-acetate) was used as the positive control, and stimulation was similarly performed at 37° C. for 48 hours. The plates were washed with PBS-T and then incubated with a biotinylated anti-mouse IFN-γ antibody or a biotinylated anti-mouse IL-4 antibody at 4° C. overnight. The plates were washed, and streptavidin alkaline phosphatase was added to each well, followed by incubation at room temperature for 2 hours. The plates were washed with PBS-T and then incubated with 5-bromo-4-chloro-3-indolyl phosphate P-toluidine salt and a nitro blue tetrazolium solution at room temperature for 30 minutes. The plates were washed with water and air-dried at room temperature, and colored spots were counted with a dissecting microscope (Zeiss, Stemi 305).
(2) Results The results were shown in FIGS. 10A and 10B. FIG. 10A shows microscopic images of representative wells of the indicated groups, and FIG. 10B shows the results of the measurement of the number of colored spots. Stimulation with KLH induced the production of IFN-γ and IL-4, and a significantly large number of splenocytes producing both IFN-γ and IL-4 in response to stimulation with KLH were observed as with treatment with the positive control ionomycin/PMA. In contrast, neither the S100A9 antigenic peptide (S100A9-epitope peptide in the figure) nor the recombinant S100A9 protein elicited any significant response as compared with non-stimulation and the KLH control group. These results show that KLH contains adequate T-cell epitopes to induce T-cell activation in the S100A9-vaccinated mice. In addition, no increase in the production of IFN-γ and IL-4 after stimulation with the S100A9 antigenic peptide or the recombinant S100A9 protein indicates that the activation of cytotoxic T-cells targeting the autologous protein S100A9 was prevented. That is, in the S100A9-vaccinated mice, Th cells are considered to predominantly differentiate into Th2-type cells capable of inducing antibody production.

Example 8

Examination of Long-Term Efficacy of S100A9 Vaccine (1) Experimental Method

Figure 11:
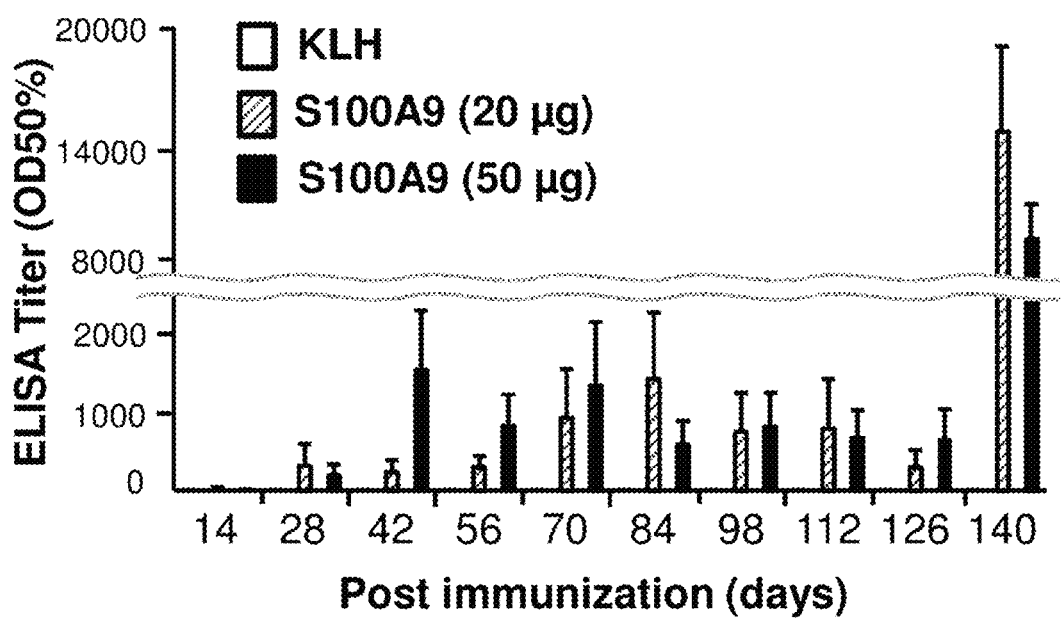
FIG. 11 shows the results of time-course measurement of the antibody titer against S100A9 in SA9001-K-vaccinated mice.

The mice in the SA9001-K vaccine low-dose group (20 µg (antigenic peptide)/mouse), in the SA9001-K vaccine high-dose group (50 µg (antigenic peptide)/mouse), and in the KLH (control) group, which were given the SA9001-K vaccine or KLH on Days 0, 14, and 28 in Example 1, were additionally vaccinated on Day 126. Blood samples were collected from the tail vein on Days 14, 28, 42, 56, 70, 84, 98, 112, 126, and 140, and the antibody titer against S100A9 was measured by ELISA as described in Example 1.
(2) Results The results are shown in FIG. 11. The antibody titer against S100A9 showed a dose-dependent increase on Days 42, 56, and 70, and a gradual reduction until Day 98. The antibody titer in the SA9001-K vaccine high-dose group was about 6 times higher than that in the SA9001-K vaccine low-dose group on Day 42. The additional vaccination on Day 126 led to a markedly increase in the antibody titer against S100A9 at 14 days after the additional vaccination (Day 140) in both the low-dose and high-dose groups. These results show that the production of the antibody against S100A9 can be sustained for at least 2 months from the last vaccination and that booster effect can be obtained by additional vaccination.

Example 9

Figure 12:
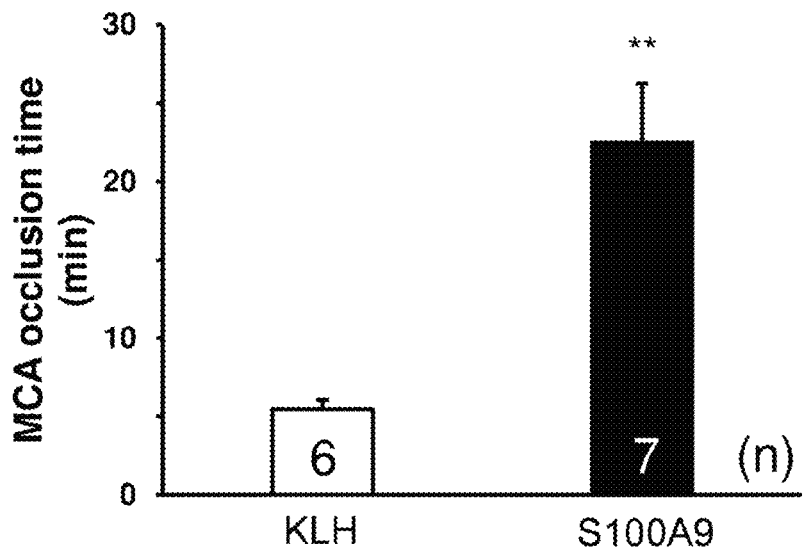
FIG. 12 shows the results of the measurement of the middle cerebral artery occlusion time after additional SA9001-K vaccination (booster immunization).

Examination of Efficacy and Safety of S100A9 Vaccine After Booster Immunization 9-1 Middle Cerebral Artery Occlusion Time
(1) Experimental Method Three weeks after the additional vaccination (booster immunization) of Example 8, the mice in the SA9001-K vaccine high-dose group and in the KLH group were subjected to a middle cerebral artery occlusion test as described in Example 2, and the occlusion time was measured.
(2) Results The results are shown in FIG. 12. The middle cerebral artery occlusion time was significantly delayed in the SA9001-K vaccine high-dose group as compared with the KLH group ($p<0.01$).
9-2 Tail Bleeding Time
(1) Experimental Method The mice which had undergone the middle cerebral artery occlusion test in 9-1 were subjected to a tail bleeding assay on the same day, and the tail bleeding time was measured as described in Example 4.

(2) Results

Figure 13:
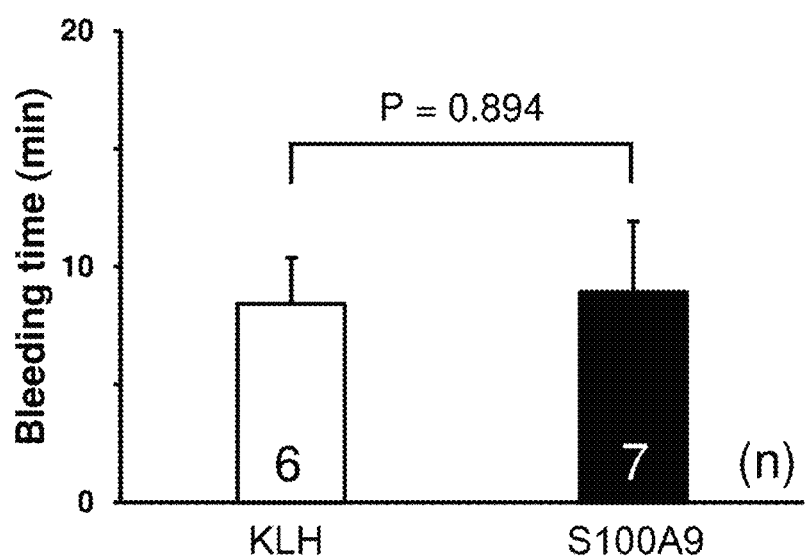
FIG. 13 shows the results of the measurement of the tail bleeding time after additional SA9001-K vaccination (booster immunization).

The results are shown in FIG. 13. No significant difference in the tail bleeding time was observed between the SA9001-K vaccine high-dose group and the KLH group.

9-3 Histopathological Examination (1) Experimental Method

After the additional vaccination (booster immunization) was performed on Day 126 in Example 8, the brain and kidney were dissected on Day 147, fixed with 4% paraformaldehyde overnight, and embedded in paraffin. The brain and kidney were cut into sections, and the sections were stained with hematoxylin/eosin. In addition, the kidney sections were stained with periodic acid-Schiff (PAS).

(2) Results

Figure 14:
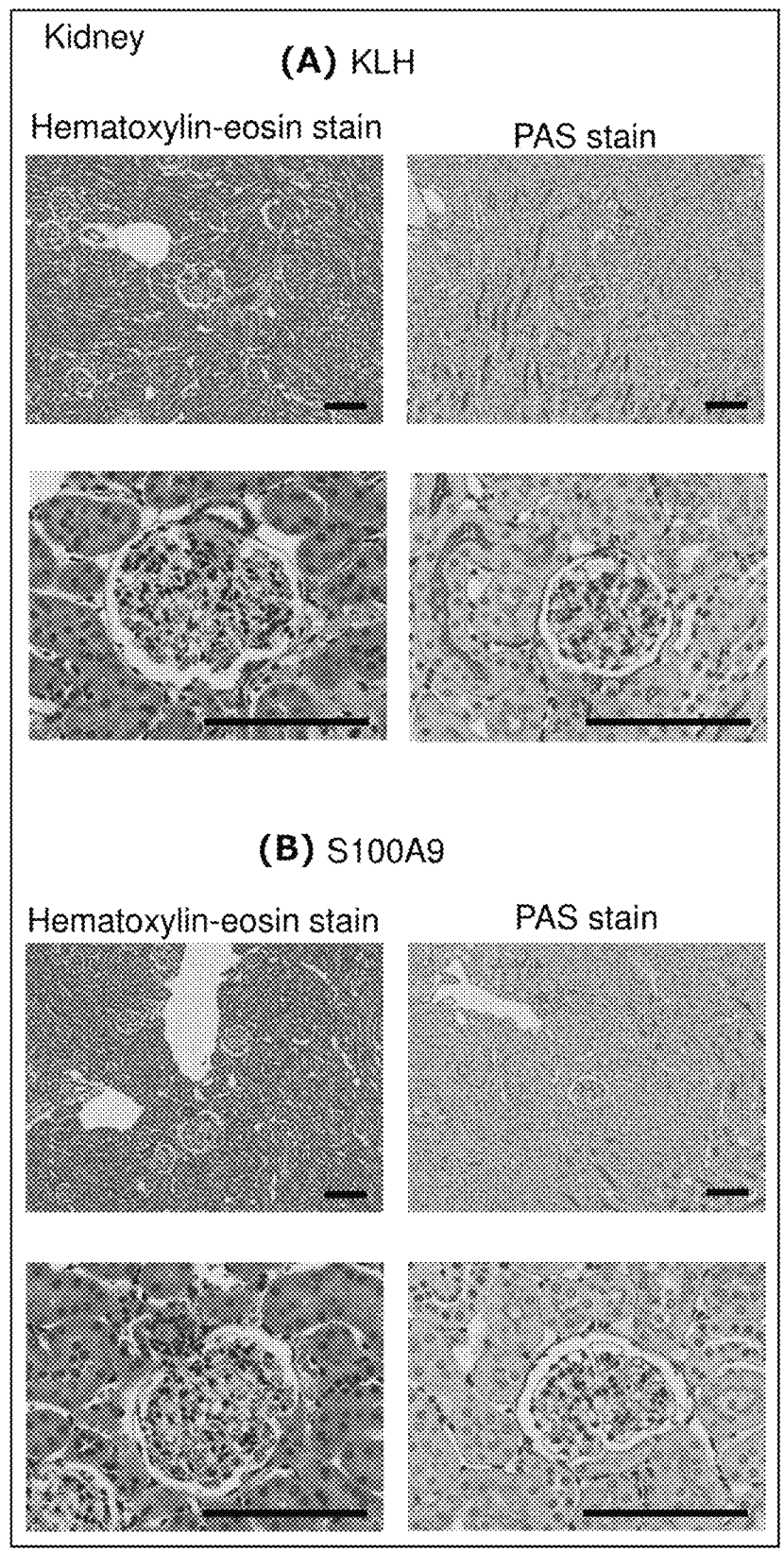
FIG. 14 shows the results of histopathological examination of the kidneys on Day 147 after the first vaccination.
Figure 15:
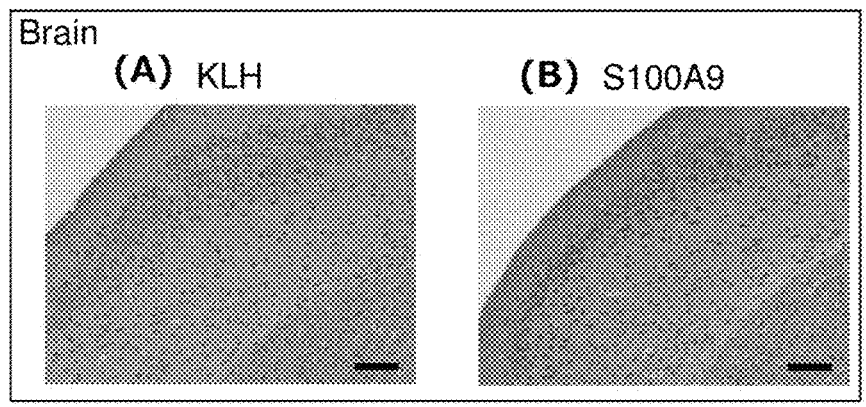
FIG. 15 shows the results of histopathological examination of the brains on Day 147 after the first vaccination.

The results for the kidney were shown in FIG. 14, and the results for the brain were shown in FIG. 15. In each panel, the scale bar marks 100 μm. No obvious pathological changes in the kidney or brain were observed. T-cell and macrophage infiltration were also not observed.

Example 10

Examination of Effect on S100A9/CD36 Signaling (1) Experimental Method

The mice in the SA9001-K vaccine high-dose group and the KLH group of Example 1 were used for the test described below. Two weeks after the final administration (Day 42), craniotomy was performed on mice as described in Example 2, and a piece of filter paper saturated with 20% ferric chloride was placed on the pia mater on the right distal middle cerebral artery for 4 minutes. After that, blood samples were collected from the inferior vena cava, and platelets were isolated. Proteins were extracted from the platelets and subjected to western blotting. An anti-JNK antibody (Cell Signaling Technology, Inc.) and an anti-phosphorylated JNK antibody (Cell Signaling Technology, Inc.) were used for western blotting.

(2) Results

Figure 16:
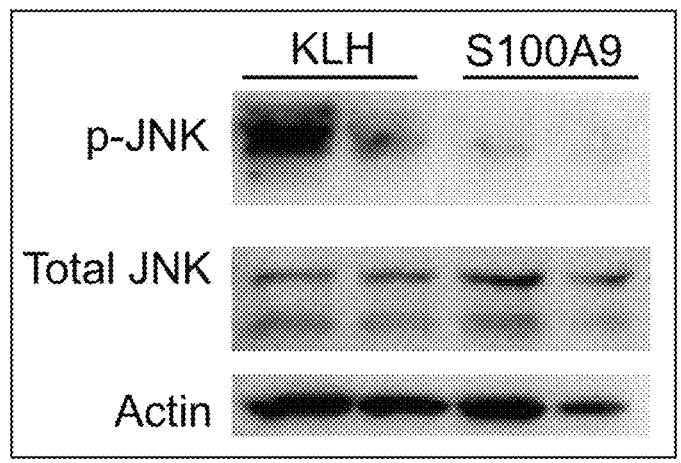
FIG. 16 shows the effect of an S100A9 vaccine on S100A9/CD36 signaling.

The results are shown in FIG. 16. The phosphorylation of JNK, which is a downstream signal of S100A9/CD36 in platelet aggregation, was inhibited in the SA9001-K vaccination group.

Example 11

Examination of Effect Against Common Carotid Artery Occlusion (1) Experimental Method The mice in the SA9001-K vaccine high-dose group and the KLH group of Example 1 were subjected to a common carotid artery occlusion test at 3 weeks after the final administration. Mice were anesthetized by inhalation of 1.4% isoflurane and placed in a supine position. An incision was made through the cervical skin to expose the right common carotid artery, and the adventitia was removed. A piece of filter paper saturated with 7.5% ferric chloride was placed on the common carotid artery for 1 minute and then removed. Blood flow was recorded with a laser speckle blood flow imager (OMEGAZONE OZ-2, OMEGAWAVE, INC.) for 30 minutes. The time at which a duration of blood flow cessation exceeding 3 minutes was confirmed was recorded as the occlusion time.

(2) Results

Figure 17:
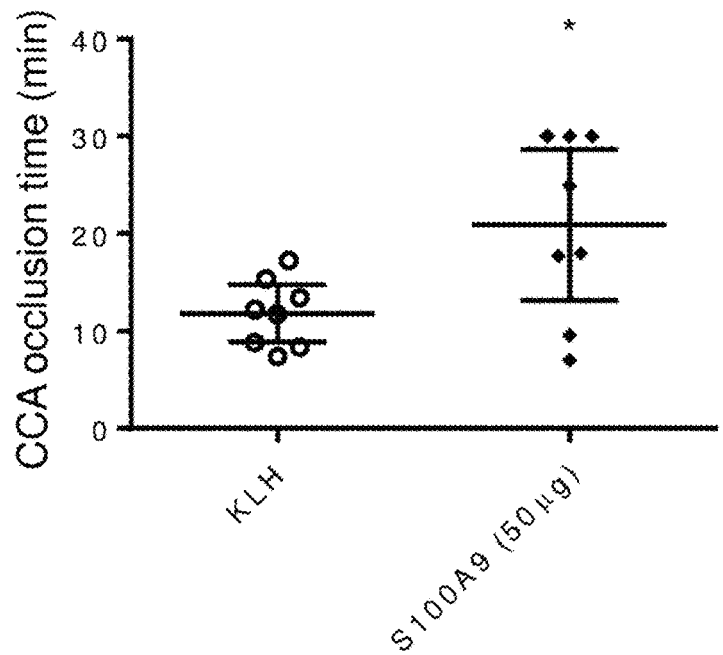
FIG. 17 shows the effect of an S100A9 vaccine against common carotid artery occlusion in common carotid artery occlusion model mice.

The results are shown in FIG. 17. The common carotid artery occlusion time was significantly prolonged in the SA9001-K vaccine group as compared with the KLH group ($p<0.05$). These results show that S100A9 vaccination is effective not only against middle cerebral artery occlusion but also common carotid artery occlusion.

Example 12

Examination of Effect Against Internal Jugular Vein Thrombosis (1) Experimental Method The mice in the SA9001-K vaccine high-dose group and the KLH group of Example 1 were subjected to an internal jugular vein thrombosis test at 3 weeks after the final administration. Mice were anesthetized by inhalation of 1.4% isoflurane and placed in a supine position. An incision was made through the cervical skin to expose the internal jugular vein. A piece of filter paper saturated with 10% ferric chloride was placed on the internal jugular vein for 3 minutes and then removed. Blood flow was recorded with a laser speckle blood flow imager (OMEGAZONE OZ-2, OMEGAWAVE, INC.) for 30 minutes. The time at which a duration of blood flow cessation exceeding 3 minutes was confirmed was recorded as the occlusion time.

(2) Results

Figure 18:
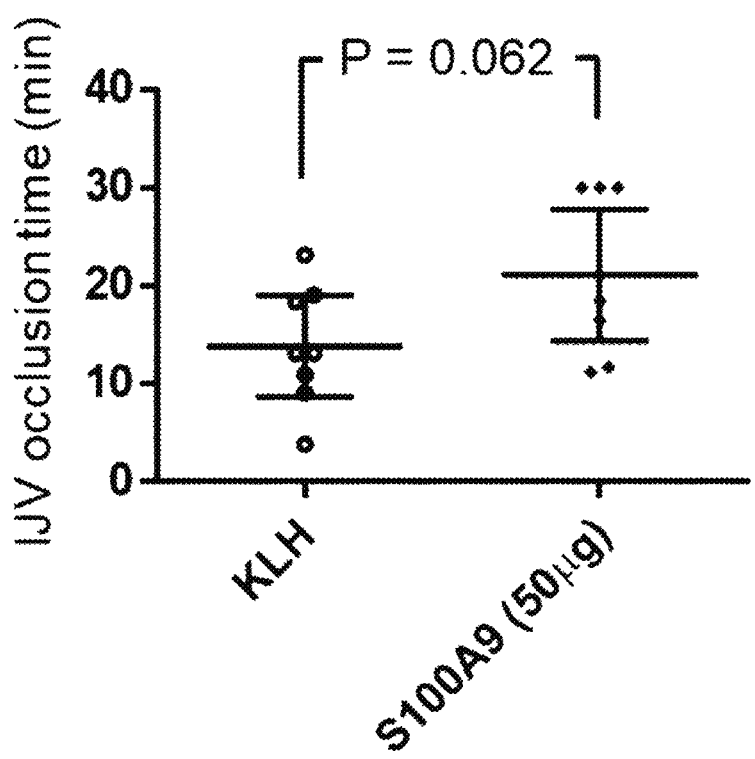
FIG. 18 shows the effect of an S100A9 vaccine against internal jugular vein occlusion in internal jugular vein thrombosis model mice.

The results are shown in FIG. 18. No significant difference was observed between the KLH group and the SA9001-K vaccine group (P=0.062), but the SA9001-K vaccine group showed a tendency to prolong the internal jugular vein occlusion time as compared with the KLH group.

Example 13

Antibody Production in Human S100A9-Vaccinated Monkeys (1) Preparation of KLH-Human S100A9 Antigenic Peptide Conjugate Vaccine A peptide consisting of the amino acid sequence (GHHHKPGLGE) represented by SEQ ID NO: 1 was synthesized by the Fmoc method using a fully-automatic solid-phase synthesizer. Cysteine was added to the C-terminus of the peptide, followed by C-terminal amidation. The obtained peptide was conjugated to KLH using EMCS (N-(6-maleimidocaproyloxy)succinimide). Hereinafter, the conjugate of the antigenic peptide of human S100A9 (SEQ ID NO: 1) and KLH is called "SA9002-K".

The conjugate of GHHHKPGLGE-C—$NH_2$ and KLH (SA9002-K) was produced in the following manner.

First, KLH modified with EMC (6-maleimidocaproyl KLH) was prepared. Specifically, a DMSO solution of N-(6-maleimidocaproyloxy)succinimide (EMCS 40 mg) was added dropwise to a solution of KLH (300 mg) in phosphate buffer (pH 8.0), and the mixture was stirred for 3 hours. Then, dialysis against a salt solution was repeated 3 times to give EMC-modified KLH. Subsequently, the peptide (6 mg) was dissolved in phosphate buffer (pH 7.0). This peptide solution was added dropwise to an EMC-modified KLH (25 mg) solution, and the mixture was stirred at room temperature overnight. Then, the mixture was subjected to dialysis against $H_2O$ 3 times, and the inner fluid was freeze-dried to give the desired product. The yield was 24 mg. Successful conjugation of the peptide to the carrier protein was confirmed by amino acid analysis (result: 49 to 62 nmol peptide/mg conjugate).

(2) Experimental Method

The experiment described below was performed in CMIC Pharma Science Co., Ltd. Two 3 to 4-year-old male cynomolgus monkeys were purchased from Hamri Co., Ltd. SA9002-K was dissolved in physiological saline such that the antigenic peptide concentration was 0.4 mg/mL. This solution was mixed with an equal amount of alum to prepare a 0.2 mg/mL human S100A9 vaccine. This human S100A9 vaccine was subcutaneously administered in a volume of 0.1 mL each at 10 sites per animal on Days 0, 14, and 28. Blood samples were collected on Day 42, and the sera were separated for antibody titer measurement.

(3) Measurement of Antibody Titer

The antibody titer against a human S100A9 vaccine and the antibody titer against a recombinant human S100A9 protein were measured by ELISA.

A conjugate of the antigenic peptide of human S100A9 (SEQ ID NO: 1) and BSA was diluted to 10 μg/mL with 50 mM carbonate buffer solution. The recombinant human S100A9 protein was diluted to 2 μg/mL with 50 mM carbonate buffer solution. Each diluted solution was added in a volume of 50 μL to the wells and incubated at 4° C. overnight. The solution in each well was discarded, and blocking was performed with 100% goat serum at room temperature for 2 hours. The monkey sera were serially diluted with 100% goat serum, added in a volume of 50 μL to the wells, and incubated at 4° C. overnight. After washing with PBS-T, Goat Anti-Monkey IgG H&L (HRP) (Abcam) was diluted with 5% skim milk, added to each well, and incubated at room temperature for 3 hours. After washing with PBS-T, TMB solution was added in a volume of 50 μL to each well and incubated in light-shielded conditions at room temperature for 30 minutes. After that, the reaction stop solution (0.5 N $H_2SO_4$) was added, and the absorbance at 450 nm was measured with a microplate reader.

(4) Results

Figure 19:
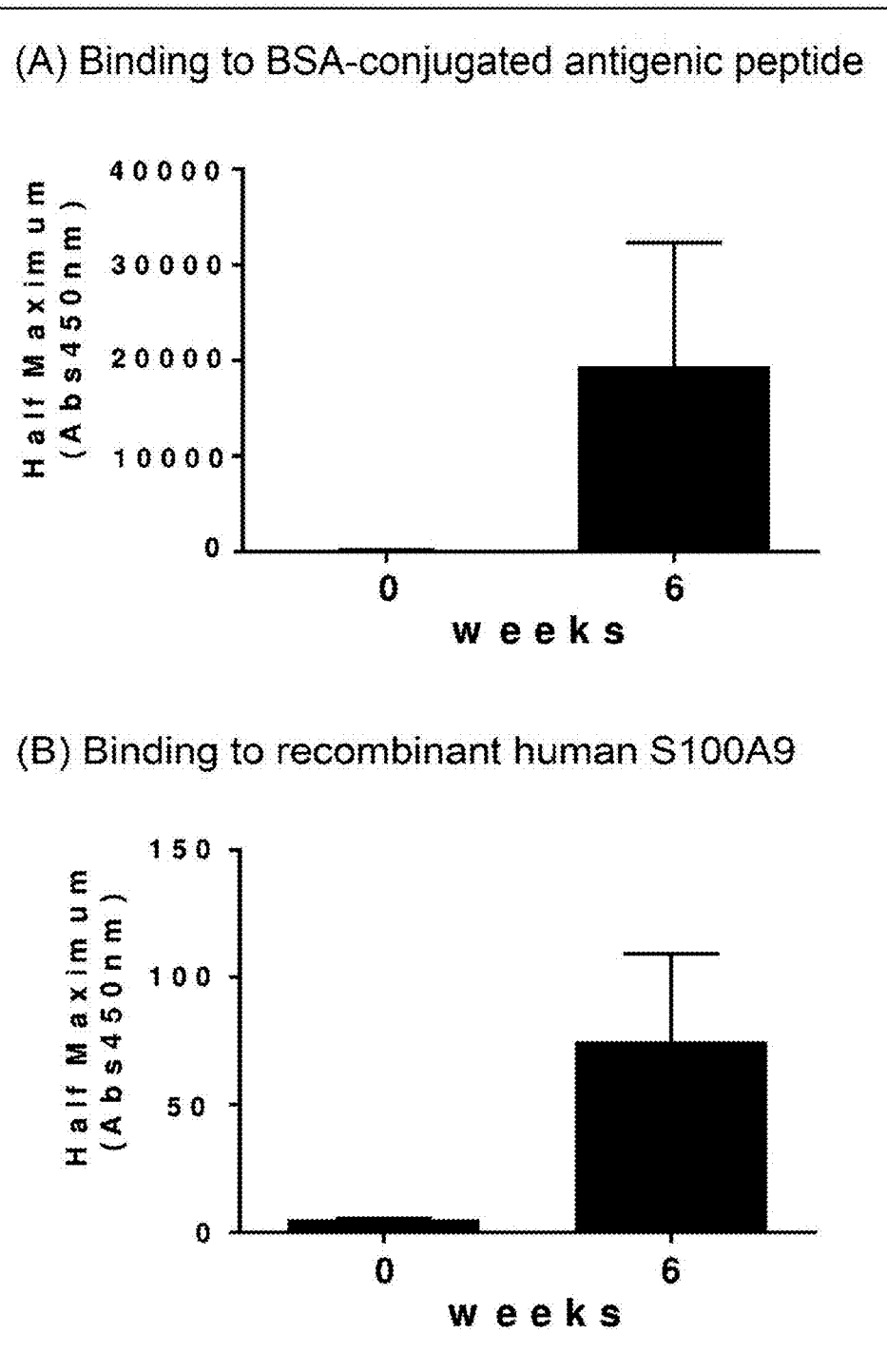
FIG. 19 shows the results of the measurement of the antibody titer in the sera of monkeys given a KLH-human S100A9 antigenic peptide conjugate (SA9002-K) vaccine.

The results are shown in FIG. 19. FIG. 19A shows the results of the measurement of the antibody titer against the conjugate of the human S100A9 antigenic peptide (SEQ ID NO: 1) and BSA. FIG. 19B shows the results of the measurement of the antibody titer against the recombinant human S100A9. The antibody titer was represented as a half-maximal antibody titer (OD 50%). Each antibody titer was markedly increased after 6 weeks.

Example 14

Antibody Production Induced by Administration of Conjugate Vaccines of Various Mouse S100A9 Antigenic Peptides and KLH Other than SA9001-K Vaccine (1) Preparation of Conjugates of Antigenic Peptides of Mouse S100A9 and KLH As the antigenic peptides of mouse S100A9, the amino acid sequence of residues 97 to 106 (ENNPRGHGHS, SEQ ID NO: 21), the amino acid sequence of residues 2 to 11 (ANKAPSQMER, SEQ ID NO: 22), and the amino acid sequence of residues 25 to 34 (RKEGHPDTLS, SEQ ID NO: 23) of the amino acid sequence of mouse S100A9 (SEQ ID NO: 4) were selected. The 3 kinds of peptides were synthesized by the Fmoc method using a fully-automatic solid-phase synthesizer. The peptide ENNPRGHGHS (SEQ ID NO: 21) was amidated at the C-terminus and conjugated to KLH via glutaraldehyde. The peptide ANKAPSQMER (SEQ ID NO: 22) was acetylated at the N-terminus, and cysteine was added to the C-terminus. After C-terminal amidation, the peptide was conjugated to KLH via EMCS. The peptide RKEGHPDTLS (SEQ ID NO: 23) was conjugated to KLH via glutaraldehyde. Hereinafter, the conjugate of the antigenic peptide of mouse S100A9 (SEQ ID NO: 21) and KLH is called "SA9003-K", the conjugate of the antigenic peptide of mouse S100A9 (SEQ ID NO: 22) and KLH is called "SA9004-K", and the conjugate of the antigenic peptide of mouse S100A9 (SEQ ID NO: 23) and KLH is called "SA9005-K".

The conjugate of ENNPRGHGHS-$NH_2$ and KLH (SA9003-K) was produced in the following manner.

Five milligrams of the peptide were dissolved in phosphate buffer (pH 8.0) and mixed with 20 mg of KLH. To this, 30 μL of a 25% aqueous glutaraldehyde solution was added dropwise, and the mixture was stirred at room temperature for 5 hours (pH 8.0). Five hours later, 0.5 mL of Tris-HCl buffer (pH 7.5) was added, and the mixture was stirred overnight. Then, the mixture was subjected to dialysis against $H_2O$ 3 times, and the inner fluid was freeze-dried to give the desired product. The yield was 26 mg. Successful conjugation of the peptide to the carrier protein was confirmed by amino acid analysis (result: 63 to 66 nmol peptide/mg conjugate).

The conjugate of Ac-ANKAPSQMER-C—$NH_2$ and KLH (SA9004-K) was produced in the following manner.

First, KLH modified with EMC (6-maleimidocaproyl KLH) was prepared. Specifically, a DMSO solution of N-(6-maleimidocaproyloxy)succinimide (EMCS 40 mg) was added dropwise to a solution of KLH (300 mg) in phosphate buffer (pH 8.0), and the mixture was stirred for 3 hours. Then, dialysis against a salt solution was repeated 3 times to give EMC-modified KLH. Subsequently, the peptide (6 mg) was dissolved in a 6 M solution of guanidine in phosphate buffer (pH 7.0). This peptide solution was added dropwise to an EMC-modified KLH (20 mg) solution, and the mixture was stirred at room temperature overnight. Then, the mixture was subjected to dialysis against $H_2O$ 3 times, and the inner fluid was freeze-dried to give the desired product. The yield was 21 mg. Successful conjugation of the peptide to the carrier protein was confirmed by amino acid analysis (result: 102 to 105 nmol peptide/mg conjugate).

The conjugate of RKEGHPDTLS and KLH (SA9005-K) was produced in the following manner.

Five milligrams of the peptide were dissolved in phosphate buffer (pH 8.0) and mixed with 25 mg of KLH. To this, 50 μL of a 25% aqueous glutaraldehyde solution was added dropwise, and the mixture was stirred at room temperature for 5 hours (pH 8.0). Five hours later, 0.5 mL of Tris-HCl buffer (pH 7.5) was added, and the mixture was stirred overnight. Then, the mixture was subjected to dialysis against $H_2O$ 3 times, and the inner fluid was freeze-dried to give the desired product. The yield was 31 mg. Successful conjugation of the peptide to the carrier protein was confirmed by amino acid analysis (result: 80 to 90 nmol peptide/mg conjugate).

(2) Experimental Method

Seven-week-old male C57BL/6J mice were purchased from CLEA Japan, Inc. The mice were assigned to 3 groups: an SA9003-K vaccine group (50 μg (antigenic peptide)/mouse), an SA9004-K vaccine group (50 μg (antigenic peptide)/mouse), and an SA9005-K vaccine group (50 μg (antigenic peptide)/mouse). The conjugates were separately mixed with an equal volume of TiterMax Gold (trade name, Titer Max) and subcutaneously administered to the mice at the ages of 8 and 10 weeks. Blood samples were collected from the tail vein before administration, and at 2, 4, 6, 8, and 10 weeks after the first administration. The sera were separated for antibody titer measurement.

The antibody titer against SA9003-K, SA9004-K or SA9005-K was measured by ELISA. More specifically, the measurement was performed using ELISA plates coated with a BSA-SA9003 conjugate (Peptide Institute), a BSA-SA9004 conjugate (Peptide Institute), or a BSA-SA9005 conjugate (Peptide Institute). An HRP-conjugated anti-mouse IgG sheep antibody (NA931V, GE Healthcare) was used for antibody detection.

(3) Results

Figure 20:
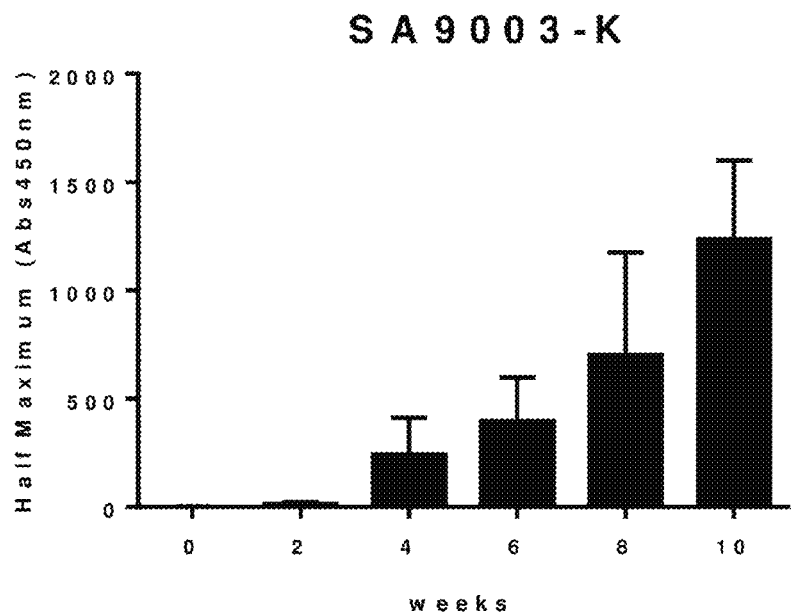
FIG. 20 shows the results of ELISA for the measurement of the antibody titer against an S100A9 antigenic peptide in the sera of mice given a conjugate (SA9003-K) vaccine of a mouse S100A9 antigenic peptide (ENNPRGHGHS, SEQ ID NO: 21) and KLH.
Figure 21:
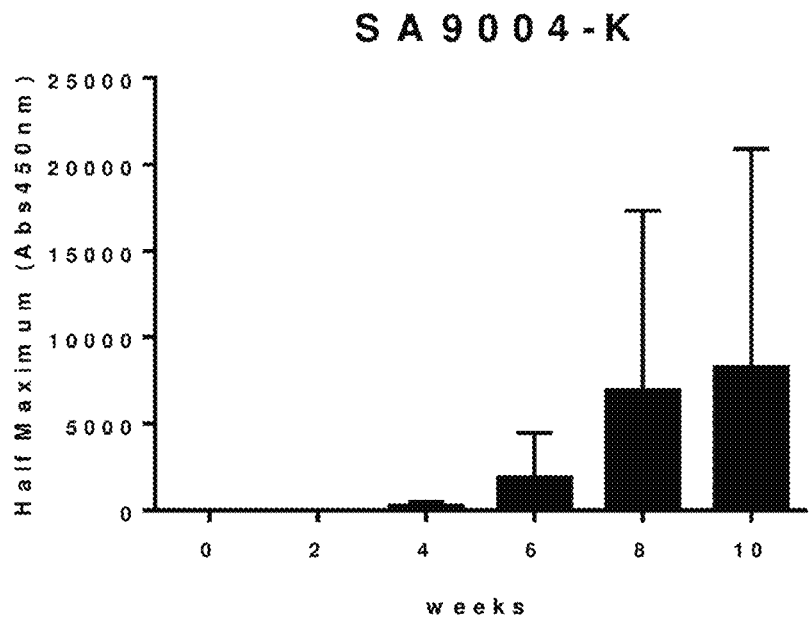
FIG. 21 shows the results of ELISA for the measurement of the antibody titer against an S100A9 antigenic peptide in the sera of mice given a conjugate (SA9004-K) vaccine of a mouse S100A9 antigenic peptide (ANKAPSQMER, SEQ ID NO: 22) and KLH.

The results for SA9003-K are shown in FIG. 20, and the results for SA9004-K are shown in FIG. 21. The antibody titer increased over time until 10 weeks after the administration of each vaccine. Similarly, the antibody titer increased over time until 10 weeks after the administration of SA9005-K.

Example 15

Effect Against Atherosclerosis (1) Experimental Method

ApoE-deficient mice (see Kawakami R et al., 2018, PLoS ONE 13 (2): e0191895) were used for the experiment described below. The ApoE-deficient mice were produced and provided by KAC Co., Ltd. The S100A9 vaccine used was SA9001-K.

Eight-week-old male ApoE-deficient mice were assigned to 2 groups: an SA9001-K vaccine group (n=5) and a control group (n=3). SA9001-K (50 μg (antigenic peptide)/mouse) was mixed with an equal amount of TiterMax Gold (trade name, Titer Max), and the mixture was subcutaneously administered to the mice assigned to the S100A9 group at the ages of 8 and 10 weeks. The mice in both groups were given free access to a high fat diet for 12 weeks at the ages of 8 to 20 weeks. Each mouse at the age of 20 weeks was perfusion-fixed with 4% paraformaldehyde under deep anesthesia, and the aorta from the heart to the iliac artery was dissected. For evaluation of atherosclerotic lesions, the aorta was stained with oil red O, and the plaque area was measured.

(2) Results

Figure 22:
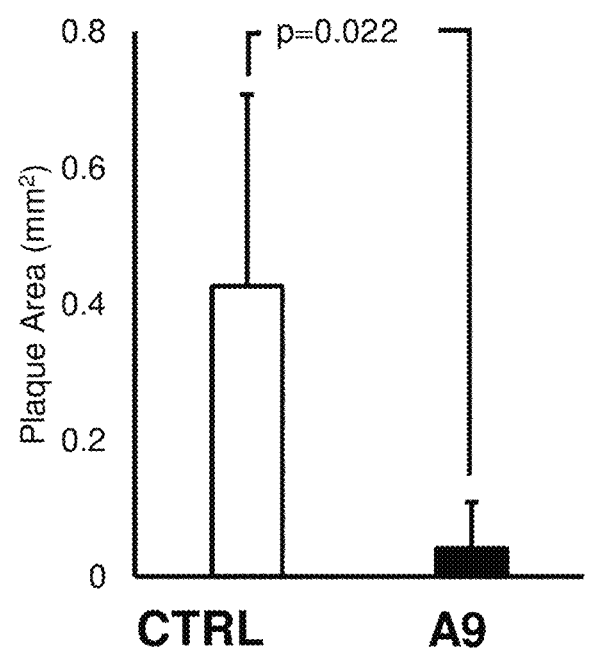
FIG. 22 shows the effect of an S100A9 vaccine on atherosclerosis as evaluated on the basis of the area of plaques formed in the artery of ApoE-deficient mice on a high fat diet.

Atherosclerotic lesions were observed in 2 of 5 animals in the SA9001-K vaccine group and in 3 of 3 animals in the control group. Each atherosclerotic lesion was observed in the aortic arch. The results of the measurement of the plaque area (the area of regions positive for oil red O staining) are shown in FIG. 22. The plaque area in the SA9001-K vaccine group (A9 in the figure) was significantly smaller than that in the control group (CTRL in the figure) (mean±SD, 0.04±0.068 ($mm^2$) vs 0.42±0.28 ($mm^2$), p=0.022). These results show that the S100A9 vaccine prevents atherosclerosis.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

---

The invention claimed is:

1. An immunogenic composition comprising an antigenic peptide that induces production of a neutralizing antibody against S100 calcium-binding protein A9 (S100A9) and a carrier protein, wherein the antigenic peptide consists of (i) 7 or more contiguous amino acids of residues 1 to 16 of SEQ ID NO: 2, (ii) 7 or more contiguous amino acids of residues 21 to 33 of SEQ ID NO: 2, or (iii) 7 or more contiguous amino acids of residues 95 to 114 of SEQ ID NO: 2.

2. The composition according to claim 1, wherein the antigenic peptide consists of SEQ ID NO: 1.

3. The composition according to claim 1, wherein the antigenic peptide consists of any of SEQ ID NOs: 6 to 20.

4. The composition according to claim 1, wherein the carrier protein is keyhole limpet hemocyanin.

5. The composition according to claim 1, further comprising an adjuvant.

6. The immunogenic composition of claim 1, wherein the antigenic peptide consists of 7 or more contiguous amino acids of residues 1 to 16 of SEQ ID NO: 2.

7. The immunogenic composition of claim 1, wherein the antigenic peptide consists of 7 or more contiguous amino acids of residues 21 to 33 of SEQ ID NO: 2.

8. The immunogenic composition of claim 1, wherein the antigenic peptide consists of 7 or more contiguous amino acids of residues 95 to 114 of SEQ ID NO: 2.

9. A method for treating thrombus formation in which S100A9 and CD36 are involved, the method comprising administering the composition according to claim 1 to an animal.

10. A method for treating thrombus formation in which S100A9 and CD36 are involved, the method comprising administering the composition according to claim 2 to an animal.

11. A method for treating thrombus formation in which S100A9 and CD36 are involved, the method comprising administering the composition according to claim 3 to an animal.

12. A method for treating thrombus formation in which S100A9 and CD36 are involved, the method comprising administering the composition according to claim 6 to an animal.

13. A method for treating thrombus formation in which S100A9 and CD36 are involved, the method comprising administering the composition according to claim 7 to an animal.

14. A method for treating thrombus formation in which S100A9 and CD36 are involved, the method comprising administering the composition according to claim 8 to an animal.

15. A method for treating arteriosclerosis in which S100A9 and CD36 are involved, the method comprising administering the composition according to claim 1 to an animal.

16. A method for treating arteriosclerosis in which S100A9 and CD36 are involved, the method comprising administering the composition according to claim 2 to an animal.

17. A method for treating arteriosclerosis in which S100A9 and CD36 are involved, the method comprising administering the composition according to claim 3 to an animal.

18. A method for treating arteriosclerosis in which S100A9 and CD36 are involved, the method comprising administering the composition according to claim 6 to an animal.

19. A method for treating arteriosclerosis in which S100A9 and CD36 are involved, the method comprising administering the composition according to claim 7 to an animal.

20. A method for treating arteriosclerosis in which S100A9 and CD36 are involved, the method comprising administering the composition according to claim 8 to an animal.

* * * * *

SEQUENCE LISTING

```
<160> NUMBER OF SEQ ID NOS: 23

<210> SEQ ID NO 1
<211> LENGTH: 10
<212> TYPE: PRT
<213> ORGANISM: Homo sapiens

<400> SEQUENCE: 1

Gly His His His Lys Pro Gly Leu Gly Glu
1               5                   10

<210> SEQ ID NO 2
<211> LENGTH: 114
<212> TYPE: PRT
<213> ORGANISM: Homo sapiens

<400> SEQUENCE: 2

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95
```

```
Gly Asp Glu Gly Pro Gly His His Lys Pro Gly Leu Gly Glu Gly
            100                 105                 110
Thr Pro

<210> SEQ ID NO 3
<211> LENGTH: 10
<212> TYPE: PRT
<213> ORGANISM: Mus musculus

<400> SEQUENCE: 3

Gly His Ser His Gly Lys Gly Cys Gly Lys
1               5                   10

<210> SEQ ID NO 4
<211> LENGTH: 113
<212> TYPE: PRT
<213> ORGANISM: Mus musculus

<400> SEQUENCE: 4

Met Ala Asn Lys Ala Pro Ser Gln Met Glu Arg Ser Ile Thr Thr Ile
1               5                   10                  15

Ile Asp Thr Phe His Gln Tyr Ser Arg Lys Glu Gly His Pro Asp Thr
            20                  25                  30

Leu Ser Lys Lys Glu Phe Arg Gln Met Val Glu Ala Gln Leu Ala Thr
        35                  40                  45

Phe Met Lys Lys Glu Lys Arg Asn Glu Ala Leu Ile Asn Asp Ile Met
    50                  55                  60

Glu Asp Leu Asp Thr Asn Gln Asp Asn Gln Leu Ser Phe Glu Glu Cys
65                  70                  75                  80

Met Met Leu Met Ala Lys Leu Ile Phe Ala Cys His Glu Lys Leu His
                85                  90                  95

Glu Asn Asn Pro Arg Gly His Gly His Ser His Gly Lys Gly Cys Gly
            100                 105                 110

Lys

<210> SEQ ID NO 5
<211> LENGTH: 9
<212> TYPE: PRT
<213> ORGANISM: Mus musculus

<400> SEQUENCE: 5

Ala Ser His Lys Asp Ser His Lys Glu
1               5

<210> SEQ ID NO 6
<211> LENGTH: 10
<212> TYPE: PRT
<213> ORGANISM: Homo sapiens

<400> SEQUENCE: 6

Met Thr Cys Lys Met Ser Gln Leu Glu Arg
1               5                   10

<210> SEQ ID NO 7
<211> LENGTH: 10
<212> TYPE: PRT
<213> ORGANISM: Homo sapiens

<400> SEQUENCE: 7

Thr Cys Lys Met Ser Gln Leu Glu Arg Asn
```

```
1               5                   10
```

<210> SEQ ID NO 8
<211> LENGTH: 10
<212> TYPE: PRT
<213> ORGANISM: Homo sapiens

<400> SEQUENCE: 8

```
Cys Lys Met Ser Gln Leu Glu Arg Asn Ile
1               5                   10
```

<210> SEQ ID NO 9
<211> LENGTH: 10
<212> TYPE: PRT
<213> ORGANISM: Homo sapiens

<400> SEQUENCE: 9

```
Lys Met Ser Gln Leu Glu Arg Asn Ile Glu
1               5                   10
```

<210> SEQ ID NO 10
<211> LENGTH: 10
<212> TYPE: PRT
<213> ORGANISM: Homo sapiens

<400> SEQUENCE: 10

```
Met Ser Gln Leu Glu Arg Asn Ile Glu Thr
1               5                   10
```

<210> SEQ ID NO 11
<211> LENGTH: 10
<212> TYPE: PRT
<213> ORGANISM: Homo sapiens

<400> SEQUENCE: 11

```
Ser Gln Leu Glu Arg Asn Ile Glu Thr Ile
1               5                   10
```

<210> SEQ ID NO 12
<211> LENGTH: 10
<212> TYPE: PRT
<213> ORGANISM: Homo sapiens

<400> SEQUENCE: 12

```
Gln Tyr Ser Val Lys Leu Gly His Pro Asp
1               5                   10
```

<210> SEQ ID NO 13
<211> LENGTH: 10
<212> TYPE: PRT
<213> ORGANISM: Homo sapiens

<400> SEQUENCE: 13

```
Tyr Ser Val Lys Leu Gly His Pro Asp Thr
1               5                   10
```

<210> SEQ ID NO 14
<211> LENGTH: 10
<212> TYPE: PRT
<213> ORGANISM: Homo sapiens

<400> SEQUENCE: 14

```
Ser Val Lys Leu Gly His Pro Asp Thr Leu
1               5                   10
```

```
<210> SEQ ID NO 15
<211> LENGTH: 10
<212> TYPE: PRT
<213> ORGANISM: Homo sapiens

<400> SEQUENCE: 15

Val Lys Leu Gly His Pro Asp Thr Leu Asn
1               5                   10

<210> SEQ ID NO 16
<211> LENGTH: 10
<212> TYPE: PRT
<213> ORGANISM: Homo sapiens

<400> SEQUENCE: 16

Gly Asp Glu Gly Pro Gly His His His Lys
1               5                   10

<210> SEQ ID NO 17
<211> LENGTH: 10
<212> TYPE: PRT
<213> ORGANISM: Homo sapiens

<400> SEQUENCE: 17

Asp Glu Gly Pro Gly His His His Lys Pro
1               5                   10

<210> SEQ ID NO 18
<211> LENGTH: 10
<212> TYPE: PRT
<213> ORGANISM: Homo sapiens

<400> SEQUENCE: 18

Glu Gly Pro Gly His His His Lys Pro Gly
1               5                   10

<210> SEQ ID NO 19
<211> LENGTH: 10
<212> TYPE: PRT
<213> ORGANISM: Homo sapiens

<400> SEQUENCE: 19

Gly Pro Gly His His His Lys Pro Gly Leu
1               5                   10

<210> SEQ ID NO 20
<211> LENGTH: 10
<212> TYPE: PRT
<213> ORGANISM: Homo sapiens

<400> SEQUENCE: 20

Pro Gly His His His Lys Pro Gly Leu Gly
1               5                   10

<210> SEQ ID NO 21
<211> LENGTH: 10
<212> TYPE: PRT
<213> ORGANISM: Mus musculus

<400> SEQUENCE: 21

Glu Asn Asn Pro Arg Gly His Gly His Ser
1               5                   10

<210> SEQ ID NO 22
```

```
<211> LENGTH: 10
<212> TYPE: PRT
<213> ORGANISM: Mus musculus

<400> SEQUENCE: 22

Ala Asn Lys Ala Pro Ser Gln Met Glu Arg
1               5                   10

<210> SEQ ID NO 23
<211> LENGTH: 10
<212> TYPE: PRT
<213> ORGANISM: Mus musculus

<400> SEQUENCE: 23

Arg Lys Glu Gly His Pro Asp Thr Leu Ser
1               5                   10
```